(12) United States Patent
Igov

(10) Patent No.: US 10,441,144 B2
(45) Date of Patent: Oct. 15, 2019

(54) ENDOSCOPE WITH SHARED WORKING CHANNEL

(71) Applicant: MORENA MEDICAL APPLICATIONS LTD., Tel Aviv (IL)

(72) Inventor: Igor Igov, Ramla (IL)

(73) Assignee: MOR RESEARCH APPLICATIONS LTD., Tel Aviv (IL)

( * ) Notice: Subject to any disclaimer, the term of this patent is extended or adjusted under 35 U.S.C. 154(b) by 247 days.

(21) Appl. No.: 15/482,824

(22) Filed: Apr. 10, 2017

(65) Prior Publication Data

US 2017/0224378 A1 Aug. 10, 2017

Related U.S. Application Data

(60) Division of application No. 14/492,297, filed on Sep. 22, 2014, now abandoned, which is a
(Continued)

(51) Int. Cl.
*A61B 1/00* (2006.01)
*A61B 1/018* (2006.01)
(Continued)

(52) U.S. Cl.
CPC ............ *A61B 1/018* (2013.01); *A61B 1/0014* (2013.01); *A61B 1/00082* (2013.01); *A61B 1/00135* (2013.01); *A61B 1/00181* (2013.01); *A61B 1/04* (2013.01); *A61B 1/05* (2013.01); *A61B 1/053* (2013.01); *A61B 1/06* (2013.01); *A61B 1/128* (2013.01); *A61B 17/0218* (2013.01); *A61B 17/320016* (2013.01); *A61B 17/320758* (2013.01); *A61B 17/3423* (2013.01); *A61B 17/3478* (2013.01); *A61B 90/30* (2016.02); *A61M 25/1011* (2013.01); *A61B 17/295* (2013.01); *A61B 18/1492* (2013.01); *A61B 90/361* (2016.02); *A61B 2017/0034* (2013.01); *A61B 2017/00269* (2013.01);
(Continued)

(58) Field of Classification Search
CPC . A61B 1/00135; A61B 1/053; A61B 1/00181; A61B 1/0014; A61B 17/0218; A61B 17/320016; A61B 2017/0034; A61B 2017/00296; A61B 17/295; A61B 18/1492
USPC .......................... 600/104, 121–123, 141, 142
See application file for complete search history.

(56) References Cited

U.S. PATENT DOCUMENTS 3,060,972 A * 10/1962 Sheldon ............... A61B 1/0055
138/120
4,796,607 A 1/1989 Allred, III et al.
(Continued)

FOREIGN PATENT DOCUMENTS

CA 2552817 8/2006
CN 101474057 7/2009
(Continued)

*Primary Examiner* — Julian W Woo
(74) *Attorney, Agent, or Firm* — Soroker Agmon Nordman

(57) ABSTRACT

A method and system are disclosed for opening a workspace inside a lumen of a living creature are disclosed. Anchors may be affixed to opposite ends of the workspace. An extender may be distance anchors apart while they are affixed to the walls of the workspace. Distancing the anchors may unfold and/or stretch the lumen in the region of the workspace.

16 Claims, 20 Drawing Sheets

Related U.S. Application Data continuation-in-part of application No. PCT/IL2014/050779, filed on Aug. 31, 2014.

(60) Provisional application No. 62/015,271, filed on Jun. 20, 2014, provisional application No. 61/988,162, filed on May 3, 2014, provisional application No. 61/910,235, filed on Nov. 29, 2013, provisional application No. 61/891,075, filed on Oct. 15, 2013, provisional application No. 61/880,941, filed on Sep. 22, 2013, provisional application No. 61/872,637, filed on Aug. 31, 2013.

(51) Int. Cl.

| | | |
|---|---|---|
| *A61B 1/04* | (2006.01) | |
| *A61B 1/06* | (2006.01) | |
| *A61B 17/02* | (2006.01) | |
| *A61B 17/34* | (2006.01) | |
| *A61M 25/10* | (2013.01) | |
| *A61B 17/32* | (2006.01) | |
| *A61B 1/05* | (2006.01) | |
| *A61B 17/3207* | (2006.01) | |
| *A61B 1/12* | (2006.01) | |
| *A61B 90/30* | (2016.01) | |
| *A61B 17/295* | (2006.01) | |
| *A61B 18/14* | (2006.01) | |
| *A61B 17/00* | (2006.01) | |
| *A61B 17/22* | (2006.01) | |
| *A61B 17/30* | (2006.01) | |
| *A61B 18/00* | (2006.01) | |
| *A61B 90/00* | (2016.01) | |

(52) U.S. Cl.
CPC ............. *A61B 2017/00287* (2013.01); *A61B 2017/00296* (2013.01); *A61B 2017/00566* (2013.01); *A61B 2017/22051* (2013.01); *A61B 2017/22065* (2013.01); *A61B 2017/22069* (2013.01); *A61B 2017/306* (2013.01); *A61B 2017/320048* (2013.01); *A61B 2017/320775* (2013.01); *A61B 2018/00029* (2013.01); *A61B 2018/00047* (2013.01); *A61B 2090/08021* (2016.02); *A61B 2090/371* (2016.02); *A61B 2217/005* (2013.01); *A61B 2217/007* (2013.01); *A61M 2025/1015* (2013.01)

(56) References Cited

U.S. PATENT DOCUMENTS

| | | | |
|---|---|---|---|
| 5,166,787 A | 11/1992 | Irion | |
| 5,217,001 A | 6/1993 | Nakao et al. | |
| 5,314,243 A | 5/1994 | McDonald et al. | |
| 5,329,887 A | 7/1994 | Ailinger et al. | |
| 5,331,947 A | 7/1994 | Shturman | |
| 5,462,529 A | 10/1995 | Simpson et al. | |
| 5,645,519 A | 7/1997 | Lee et al. | |
| 6,606,515 B1 | 8/2003 | Windheuser et al. | |
| 6,895,304 B2 | 5/2005 | Spano, Jr. et al. | |
| 6,996,455 B2 | 2/2006 | Eggenberger et al. | |
| 7,006,894 B2 | 2/2006 | De La Huerga | |
| 7,083,594 B2 | 8/2006 | Coppi | |
| 7,413,543 B2 | 8/2008 | Banik et al. | |
| 7,431,694 B2 | 10/2008 | Stefanchik et al. | |
| 7,615,003 B2 * | 11/2009 | Stefanchik ......... A61B 1/00073 600/104 |
| 7,615,005 B2 | 11/2009 | Stefanchik et al. | |
| 7,698,019 B2 | 4/2010 | Moncrief et al. | |
| 7,729,738 B2 | 6/2010 | Flaherty et al. | |
| 7,762,949 B2 | 7/2010 | Nakao | |
| 7,865,263 B2 | 1/2011 | Spano et al. | |
| 7,908,827 B2 | 3/2011 | Knoth | |
| 7,914,448 B2 | 3/2011 | Bob et al. | |
| 7,958,701 B2 | 6/2011 | Knoth | |
| 8,006,903 B2 | 8/2011 | Braun et al. | |
| 8,131,562 B2 | 3/2012 | Hernandez et al. | |
| 8,246,646 B2 | 8/2012 | Kambin et al. | |
| 8,269,828 B2 | 9/2012 | Miller et al. | |
| 8,398,540 B2 | 3/2013 | Hassidov et al. | |
| 8,602,980 B2 | 12/2013 | Bassan et al. | |
| 8,731,966 B2 | 5/2014 | Breitenstein et al. | |
| 9,084,621 B2 * | 7/2015 | Weitzner ............ A61B 1/0014 |
| 9,205,234 B2 | 12/2015 | Hardin | |
| 10,292,575 B2 * | 5/2019 | Surti ............... A61B 1/00135 |
| 2001/0002448 A1 | 5/2001 | Wilson et al. | |
| 2001/0048027 A1 | 12/2001 | Walsh | |
| 2003/0055685 A1 | 3/2003 | Cobb et al. | |
| 2004/0092794 A1 | 5/2004 | Chin | |
| 2004/0230095 A1 | 11/2004 | Stefanchik et al. | |
| 2005/0085691 A1 | 4/2005 | Nakao | |
| 2005/0085695 A1 | 4/2005 | Shener et al. | |
| 2005/0272976 A1 | 12/2005 | Tanaka et al. | |
| 2007/0106113 A1 | 5/2007 | Ravo | |
| 2008/0097292 A1 | 4/2008 | Cabiri et al. | |
| 2008/0262649 A1 | 10/2008 | Allinson et al. | |
| 2010/0268028 A1 | 10/2010 | Ghabrial | |
| 2011/0105845 A1 | 5/2011 | Gordon et al. | |
| 2012/0035416 A1 | 2/2012 | Fernandez et al. | |
| 2012/0232339 A1 | 9/2012 | Csiky | |
| 2012/0265552 A1 | 10/2012 | Rabinowitz et al. | |
| 2012/0277731 A1 | 11/2012 | Boutillette | |
| 2013/0131451 A1 | 5/2013 | Dillinger et al. | |
| 2013/0296647 A1 * | 11/2013 | Mayse ............... A61B 18/1492 600/104 |
| 2013/0296771 A1 | 11/2013 | Shtul et al. | |
| 2015/0080933 A1 | 3/2015 | Igov | |
| 2015/0213224 A1 | 7/2015 | Amarasingham et al. | |
| 2015/0265143 A1 | 9/2015 | Yoon | |
| 2016/0174814 A1 | 6/2016 | Igov | |

FOREIGN PATENT DOCUMENTS

| | | |
|---|---|---|
| CN | 101779947 | 7/2010 |
| CN | 101803900 | 8/2010 |
| CN | 103027660 | 4/2013 |
| DE | 102005031304 | 1/2007 |
| EP | 1955643 | 8/2008 |
| GB | 2502767 | 12/2013 |
| KR | 1150350 | 6/2012 |
| KR | 10-2012-0111603 | 10/2012 |
| WO | 2004010858 | 2/2004 |
| WO | 2014063007 | 4/2014 |
| WO | 2015029040 | 3/2015 |
| WO | 2015123540 | 8/2015 |

* cited by examiner

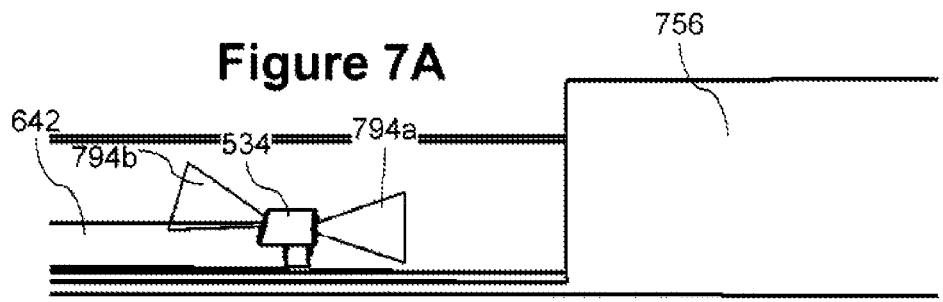
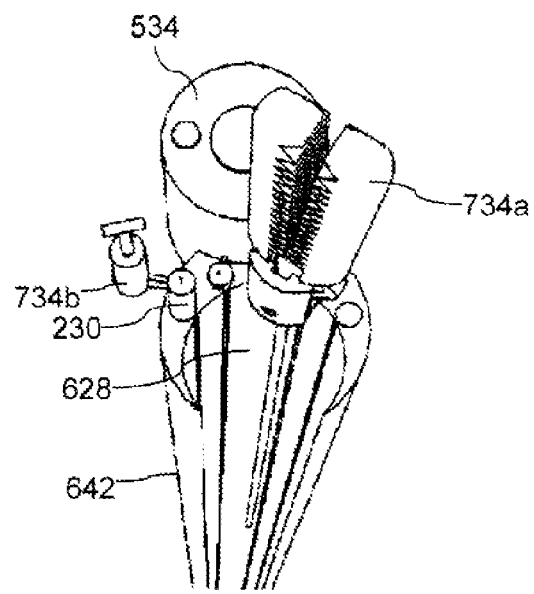

ENDOSCOPE WITH SHARED WORKING CHANNEL

RELATED APPLICATIONS

This application is a Divisional of U.S. patent application Ser. No. 14/492,297 filed on Sep. 22, 2014, which is a Continuation-in-Part (CIP) of PCT Patent Application No. PCT/IL2014/050779 having International filing date of Aug. 31, 2014, which claims the benefit of priority under 35 USC § 119(e) of U.S. Provisional Patent Application Nos. 61/872,637 filed on Aug. 31, 2013, 61/880,941 filed on Sep. 22, 2013, 61/891,075 filed on Oct. 15, 2013, 61/910,235 filed on Nov. 29, 2013, 61/988,162 filed on May 3, 2014 and 62/015,271 filed on Jun. 20, 2014. The contents of the above applications are all incorporated by reference as if fully set forth herein in their entirety.

FIELD AND BACKGROUND OF THE INVENTION

The present invention, in some embodiments thereof, relates to a system for opening a working space in a lumen of a living creature and, more particularly, but not exclusively, to a dissector for unfolding a fold in a lumen of a living creature.

U.S. Pat. No. 5,725,545 discloses a balloon dissector in which an elastic balloon is positioned on an exterior portion of a rigid tube. The tube is inserted into the patient and then a medium, such as saline solution, is inserted into the hollow tube.

The medium is communicated to an interior portion of the elastic balloon causing the balloon to expand and dissect tissue in the area. This dissection permits a subsequent surgical procedure to be performed at the site. Since the tube is rigid, one end of the tube is preferably shaped as a dissector. The rigid tube is graspable by the surgeon and is used as an instrument during its insertion into the site. The rigid tube, in one embodiment of the invention, is rigidly affixed to a syringe containing the medium so that the syringe/tube form one unit which is manipulated by the surgeon.

U.S. Pat. No. 8,246,646 discloses a balloon dissector passed through a tube and expanded. Following dissection by expansion of the balloon, the balloon is contracted, the tube is advanced, and the dissected tissue is spread by moving the blades apart from each other. The balloon dissector is withdrawn and another instrument is then introduced to carry out surgery on the anatomical structure exposed by the dissection and spreading steps.

U.S. Pat. No. 7,431,694 discloses a guide system for use with an endoscope, and a method of use. The guide system can include a track, in the form of a rail, and a mating member for engaging the rail. The guide system can also include an accessory, such as an accessory guide tube through which a medical instrument can be carried external of the endoscope. An end cap can be provided to support the track relative to the distal end of the endoscope.

Additional background art includes Canadian Patent No. 2552817, U.S. Pat. No. 5,166,787, U.S. Published Patent Application No. 2005/0272976 to Tanaka, U.S. Pat. Nos. 7,413,543, 4,796,607, 8,269,828, U.S. Published Patent Application No. 2013/0131451, U.S. Pat. Nos. 7,914,448, 5,166,787.

SUMMARY OF THE INVENTION

According to an aspect of some embodiments of the present invention there is provided a system for opening a workspace inside a lumen of a living creature comprising: an extender fitting through a channel of a catheter; a tool for performing a function in the lumen; a first anchor mounted proximal to the tool configured for attachment to a wall of the lumen; a second anchor mounted to the extender distal to the tool, the anchor configured for attachment to a wall of the lumen; and wherein the extender is configured for expanding a distance between the first anchor and the second anchor.

According to some embodiments of the invention, the tool is mounted to the extender.

According to some embodiments of the invention, the first anchor is mounted to the extender.

According to some embodiments of the invention, the system further includes a shaft extending through a channel of the a catheter and where the system is mounted on a distal portion of the shaft.

According to some embodiments of the invention, the first anchor includes a balloon.

According to some embodiments of the invention, the first anchor is mounted on the catheter proximal to a distal opening thereof.

According to some embodiments of the invention, the extender includes a stiff shaft extending a distally from the distal opening.

According to some embodiments of the invention, the catheter includes a guide and the stiff shaft is conveyed along the guide.

According to some embodiments of the invention, the stiff extender extends from a distal end of the catheter.

According to some embodiments of the invention, the stiff shaft extends from a fixed point in a cross section of the distal end of the catheter.

According to some embodiments of the invention, a distal portion of the stiff shaft is extensible.

According to some embodiments of the invention, the stiff shaft has two states: a flexible state and a stiff state, wherein the stiff shaft resists buckling along the longitudinal axis of the catheter.

According to some embodiments of the invention, the system further includes a stiffness controller for adjusting a stiffness of a distal portion of the extender from a proximal end of the catheter.

According to some embodiments of the invention, the system further includes a sensor for sensing an opening of a fold resulting from the expanding and stopping the expanding in response to the expanding.

According to an aspect of some embodiments of the present invention there is provided a method of opening a workspace in a lumen of a living creature comprising: securing a first anchor reversibly to a wall of the lumen at a first location; securing a second anchor reversibly to a wall of the lumen at a second location; and expanding a distance between the first anchor and the second anchor while the first anchor and the second anchor are secured to the first location and the second location thereby stretching the lumen between the first location and the second location.

According to some embodiments of the invention, the method further includes inserting a distal end of a catheter into the lumen and wherein the securing of the first anchor is to the first location distal to a distal opening of the catheter and the securing of the second anchor is to the second location proximal to the distal opening of the catheter.

According to some embodiments of the invention, the first location is on a first side of a fold of the lumen and the second location is on a second side of said fold and further including: opening the fold by the expanding of the distance between the anchors.

According to some embodiments of the invention, the method further includes detecting the unfolding; and stopping the expanding is response to the detecting.

According to some embodiments of the invention, a line joining from the first location to the second location is substantially perpendicular to the fold.

According to an aspect of some embodiments of the present invention there is provided a frame for a catheter comprising: a series of frame elements arranged along the length of a distal portion of the catheter, the flame elements defining at least one channel passing longitudinally along the catheter an articulated spine located entirely in a continuous region of less than one eighth a cross section of the catheter, the spine including a series of spacers defining a distance between the frame elements in the continuous region; and a steering element controlled from a proximal end of the catheter for adjusting a longitudinal spacing between the frame elements in the cross section of the catheter outside the continuous region of the spine.

According to some embodiments of the invention, a bending axis of the catheter in the distal portion passes through the spine.

According to some embodiments of the invention, the frame elements further define at least one more channel passing longitudinally along the catheter from the proximal end to the distal end.

According to some embodiments of the invention, the channel and the at least one more channel communicate through a longitudinal slit between the channel and the at least one more channel.

According to some embodiments of the invention, the channel has a longitudinal split communicating with an outside of the catheter.

According to some embodiments of the invention, a width of the channel is at least one half the width if the catheter.

According to an aspect of some embodiments of the present invention there is provided a system for cooling a heat emitting tool in a lumen of a living creature comprising: a fluid flow channel including a distal opening inside a lumen of living creature and a proximal opening outside of the living creature; and a heat exchanger in thermal communication with the tool, the heat exchanger disposed in a flow path of the flow channel.

According to some embodiments of the invention, the heat exchanger is located between the proximal opening and the distal opening.

According to some embodiments of the invention, the system further includes a housing surrounding the heat emitting tool on at least three sides, the housing including: an inflow opening, an outflow opening and a space for fluid flow between the inflow opening and the outflow opening, the space surrounding the heat emitting tool on at least three sides.

According to an aspect of some embodiments of the present invention there is provided a method of cooling a tool using a catheter having a distal opening inside a lumen of a living creature comprising: providing a heat exchanger in a fluid flow path of the catheter and in thermal communication with the tool; selecting a flow rate and temperature of a fluid to achieve a desired cooling of the heat transfer surface and serve a medicinal function; pumping the fluid at the flow rate from a proximal end of the catheter over the heat exchanger at the temperature; and releasing the liquid into the lumen after the transferring.

According to some embodiments of the invention, composition of the liquid includes at least 50% of at least one material selected from the group consisting of carbon dioxide, nitrogen, barium sulfate, and water.

According to some embodiments of the invention, the lumen is an intestine and the fluid is a gas and the flow rate is between 20 to 100 ml/min.

According to some embodiments of the invention, the selecting also includes selecting a concentration to serve the medicinal function at the flow rate.

According to some embodiments of the invention, balancing an inflow rate and an outflow rate to achieve the desired cooling rate and net flow rate.

According to an aspect of some embodiments of the present invention there is provided a system for suctioning material through a catheter channel from a lumen in a living creature comprising: a grinder having dimensions smaller than a cross section of the channel for fitting through the channel; a support located proximally to the grinder for conveying the grinder through the channel, the support aligning the grinder with an axis of the channel and supporting the tool near a distal opening of the channel for breaking up lumps entering the distal opening.

According to some embodiments of the invention, the support includes a shaft of length greater than the channel and wherein the shaft configured for rotating with respect to the channel and wherein the grinder is operationally connected to a distal portion the shaft for receiving rotational energy therefrom.

According to some embodiments of the invention, the system further includes a motor connected to a proximal portion of the shaft for rotating the shaft.

According to some embodiments of the invention, the support defines sub-channels for fluid flow from the distal opening to a proximal opening of the channel.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 7A-C are perspective views of tools and a multi-lumen catheter in use for removing a growth (for example a polyp) in accordance with an embodiment of the current invention;

DESCRIPTION OF SPECIFIC EMBODIMENTS OF THE INVENTION

Figure 1:
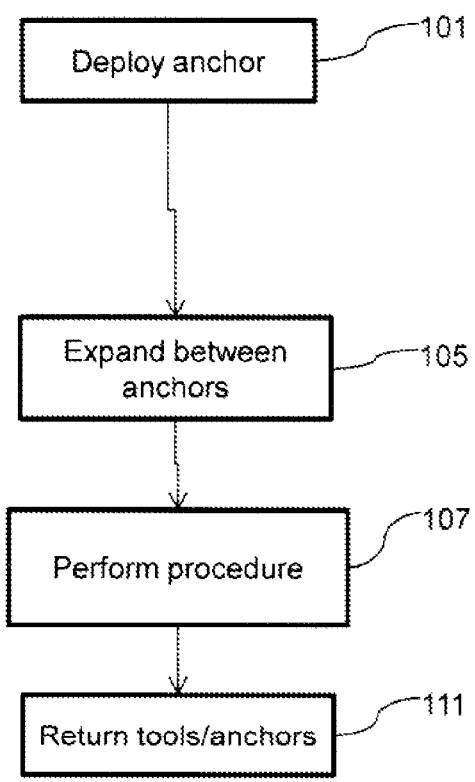
FIG. 1 is a flowchart illustrating a method of opening a workspace in a lumen of a living creature in accordance with some embodiments of the current invention.

The present invention, in some embodiments thereof, relates to a system for controlling tools in a lumen of a living creature and, more particularly, but not exclusively, to a catheter for conveying one or more tools through a shared working channel.

Overview

Method for Stretching a Lumen

An aspect of some embodiments of the current invention relates to a method for opening a workspace inside a lumen in a living creature. For example, folds and/or protrusions within a lumen may obscure view and/or access to an object. Optionally, the tool may include an anchors deployed at two points (for example proximally and/or distally of the work space). For example two anchors may be anchored to a wall of the lumen and then distanced one from the other stretching the lumen and/or removing folds from the wall of the lumen. Optionally a tool to open the workspace is deployed from a catheter. For example the tool may include a balloon. Expanding the balloon may for example open the lumen laterally.

System for Cooling a Tool

An aspect of some embodiments of the current invention relates to a system for cooling a tool inside a body of a living creature. In some embodiments, coolant (for example a fluid including for example a liquid and/or a gas) may be transferred to cool the tool (for example a tool may include a camera and/or a light source). Optionally the tool may be inside a catheter inserted into the living creature and/or the tool may be inside a lumen of the living creature. The coolant may come from outside the living creature and/or exit to the lumen inside the living creature. For example air may be used to cool the tool and/or exit into an intestine. Optionally the fluid may serve a function inside the living creature. For example a gas may serve to inflate the intestine during an endoscopic procedure. Alternatively or additionally, fluid drained and/or suctioned from the lumen and/or fluid exiting the lumen may be used for cooling a tool.

In some embodiments, a heat sink may optionally be provided inside the tool and/or outside the tool. In some embodiments cooling fluid (for example water and/or saline solution and/or air) may be pumped from outside the living creature and pass into the living creature. Alternatively or additionally cooling fluid may be pumped into the living creature and/or retrieved back outside of the living creature for disposal.

Alternatively or additionally cooling fluid may be recycled. In some embodiments cooling fluid may pass through a catheter and/or a carriage supporting the tool. In some embodiments cooling fluid may pass through a guide channel of the catheter and/or a working channel of the catheter. For example, the tool may be inserted through the working channel and/or the fluid may be supplied through a guide channel.

In some embodiments, a fluid source may be connected to a tool for cooling.

The fluid used for cooling the tool may optionally be used for rinsing or cleaning of objects inside the lumen.

Grinder for Suctioned Materials

An aspect of some embodiments of the present invention relates to a grinder.

Optionally the grinder eliminates potentially clogging materials from fluids suctioned from of a lumen of a living to creature to a catheter. The grinder may include a rotating blade supported by a carriage. The blade and carriage may optionally pass from outside the living creature into a proximal opening of a catheter and/or be conveyed through a channel of the catheter to a distal opening of the catheter. Optionally the distal opening of the catheter may be located inside a lumen of the living creature. Optionally the blade may be passed out the distal opening of the catheter. For example the blade may grind material in the flow entering the catheter channel before the material enters the channel. Alternatively or additionally, the blade may grind material as it enters and/or after it enters the catheter channel.

In some embodiments, the carriage may support the rotating blade. For example the carriage may maintain the rotating blade aligned with the entrance of the channel. Optionally the rotating blade is mounted on a shaft that rotates with respect to the carriage. Alternatively or additionally, the carriage may rotate with the rotating blade. Optionally rotational energy is supplied from outside the proximal end of the catheter (for example by rotating a shaft which passes through the catheter channel to the rotating blade).

In some embodiments suctioned material passes from the lumen into a distal opening of the catheter, along a channel of the catheter and/or out a proximal opening of the catheter. Optionally the material may pass along the channel through which the carriage and/or rotating blade passed. Optionally the carriage remains within the channel while the rotating blade grinds material entering the channel. For example material may pass through a channel in the carriage. Alternatively or additionally, the suctioned material may pass through a sub-channel between the carriage and the walls of the channel.

Frame for Catheter with an Open Channel

An aspect of some embodiments of present invention relates to a frame and/or skeleton for a catheter. Optionally the frame includes a flexible spine connecting a series of elements supporting the cross section of the catheter. The spine may, for example, preserve spacing between the elements along the axis of the spine.

Optionally the spine runs along one side of the catheter. Optionally the spine occupies a small portion of the cross section of the catheter. Optionally the catheter includes an open channel and/or a large working channel.

In some embodiments the spine is made up of a series of elements. The elements of the spine may, for example, be connected by joints and/or hinges.

Optionally the joints joining different elements are oriented in different directions. In some embodiments, the spine as a whole can optionally be bent in any direction. The elements of the frame optionally support the cross sectional form of the catheter. The distal end of the catheter may be steered from the proximal end. For example steering may be by a manual means, for example steering cables. Optionally the catheter may include a working channel and/or one or more guide channels.

Optionally, there may be a longitudinal slit providing communication between the working channel and the space outside the catheter. Alternatively or additionally, there may be a longitudinal split providing communication between the working channel and one or more of the guides. Alternatively or additionally, there may be a longitudinal slit providing communication between a guide and the space outside the catheter.

Magnetic Steering for Catheter

An aspect of some embodiments of the current invention relates to steering a catheter with remotely controlled actuators. For example actuators may include magnets controlling the angle between elements of the catheter frame. For example the actuators may interconnect between spinal spacers and/or frame elements and/or ribs of the catheter.

Optional Features

In some embodiments, the working channel may include a distal opening and/or a proximal opening. Optionally, in operation the proximal opening is accessible from the outside the living creature and/or the distal opening is exposed to the lumen.

For example, the working channel may be wide enough for passing a tool and/or a fluid through the proximal opening, along the length of the working channel to the distal opening and/or into the lumen. Each guide may include, for example, a narrow channel and/or a track running along all and/or part of the length of the working channel. Optionally a guide channel and/or a working channel may have a circular cross section. Alternatively or additionally a guide channel and/or a working channel may have a non-circular cross section (for example semi-circular, rectangular, triangular, etc.).

In some embodiments, a catheter may include one or more working channels.

Optionally a working channel has a closed perimeter. Alternatively or additionally, a working channel may be open over a portion of its length. In some embodiments, the working channel may be located in the center of the catheter. Alternatively or additionally the working channel may be located off center. In some embodiments, a catheter may include multiple working channels and/or guides.

For the sake of the disclosure, unless specified otherwise, the term catheter may include various kinds of catheters and/or endoscopes for example an encephaloscope, a laryngoscope, an esophagoscope, a thoracoscope, an angioscope, a nephroscope, a colonoscope, a proctoscope, an arthroscope, a rhinoscope, an esophagoscope, a bronchoscope, a mediastinoscope, a gastroscope, a laparoscope, an amnioscope, a cystoscope, and/or a hysteroscope, a urinary catheter, a nephritic catheter, an abdominal catheter, a venous catheter, an arterial catheter, an intracranial catheter, an epidural catheter, a tracheal tube, a central venous catheter, a Swan-Ganz catheter, en embryo transfer catheter, an umbilical line, a Tuohy-Borst adapter, an intrauterine catheter and/or a Quinton catheter. The size (for example the cross sectional area and/or the length) and/or form of the catheter may optionally vary. For example the size and/or form of a catheter may vary according to the type of catheter.

For example, a colonoscope, may have a length ranging between 130 to 250 cm and/or longer and/or have a working channel cross sectional area ranging between 3 to 5 $mm^2$ and/or between 5 to 10 $mm^2$ and/or between 10 to 15 $mm^2$ and/or between 15 to 25 $mm^2$ and/or have a guide channel cross sectional area ranging between 0.1 to 1 $mm^2$ and/or between 1 to 10 $mm^2$ and/or between 10 to 15 $mm^2$ and/or between 15 to 50 $mm^2$. A urinary catheter may for example have a length ranging between 20 to 25 cm and/or 25 to 40 cm and/or have a cross sectional area of a working channel ranging between 1 to 4 $mm^2$ and/or between 4 to 20 $mm^2$ and/or between 20 to 40 $mm^2$ and/or between 40 to 60 $mm^2$ and/or have a cross sectional area of a guide channel ranging between 0.1 to 1 $mm^2$, and/or between 1 to 5 $mm^2$, and/or between 5 to 30 $mm^2$.

For the sake of the current disclosure, the term distal portion of a catheter may mean for example the most distal half of the catheter and/or the most distal quarter of the catheter and/or the most distal ⅛ of the catheter and/or the most distal ¹/₁₀ of the catheter and/or the most distal portion of the catheter of length ranging between 1 and 10 cm and/or ranging between 1 mm and 1 cm.

For the sake of the current disclosure, the proximal portion of a catheter may be defined for example as the most proximal half of the catheter and/or the most proximal quarter of the catheter and/or the most proximal ⅛ of the catheter and/or the most proximal ¹/₁₀ of the catheter and/or the most proximal portion of the catheter of length ranging between 1 and 10 cm and/or ranging between 1 mm and 1 cm.

In some embodiments, the cross sectional area of a working channel may range between 90% to ½ the cross area of the catheter and/or between ½ and ¼ the cross area of the catheter and/or between ¼ and ⅑ the cross area of the catheter and/or between ⅑ and ¹/₂₅ the cross area of the catheter and/or between ¹/₂₅ and ¹/₁₀₀ the cross area of the catheter. Unless stated otherwise, as used herein, the ratio of cross section of a working channel to the cross section of the catheter refers to ratio of the minimal cross section of the channel between a proximal and a distal opening of the channel to the minimal cross sectional area of the catheter between the same openings.

Alternatively or additionally, the ratio of cross sectional area of the working channel to the cross sectional area of the catheter may refer to the minimal local ratio of the cross sectional areas at any location between a proximal opening of the channel and a distal opening of the channel. Alternatively, the ratio of cross section of a working channel to the cross section of the catheter may refer to ratio of the maximum cross section of the channel between a proximal and a distal opening of the channel to the maximum cross sectional area of the catheter between the same openings.

Alternatively or additionally, the ratio of cross sectional area of the working channel to the cross sectional area of the catheter may refer to the maximum local ratio of the cross sectional areas at any location between a proximal opening of the channel and a distal opening of the channel.

In some embodiments one or more guides may run along an inner wall of the working channel. Optionally the cross section of the working channel will be greater than the cross section of a guide associated with the working channel. For example a catheter and/or sleeve may include 1 guide and/or 2 guides and/or 3 guides and/or 4 guides and/or 5 guides and/or 6 guides and/or 7 to 10 guides and/or 10 to 15 guides.

Alternatively, one or more guides may run along an outer surface of the catheter. In some embodiments, a guide may extend beyond the catheter body. For example a guide may run along the length of a working channel and/or extend out an opening of the working channel. Alternatively or additionally, a carriage may be connected to a guide. The tool may be connected to the carriage. The carriage may extend beyond the guide, for example, the guide may be inside the working channel of the catheter while the carriage and/or the tool may extend out of the working channel.

For example the distance that a tool may extend beyond the distal end of the working may range over many values and/or depend on the kind of catheter. For example a tool may extend out from an endoscope a distance of less than one outer width of the endoscope and/or between one to five times the outer width of the endoscope and/or between 5 to 20 times the outer width of the endoscope and/or more.

A carriage is optionally controlled by a physical manipulation by a user (for example a carriage may have a handle for manipulation by a user outside the lumen and/or a connection to the carriage and/or the tool inside the lumen). Alternatively or additionally a carriage may be self propelled (for example by an actuator). For example, the carriage and/or the guide and/or the tool may include an actuator. The actuator optionally manipulates the tool and/or the carriage. The actuator may be controlled, for example by an on-board processor and/or a remote control unit.

In some embodiments, a carriage and/or tool may be introduced into the working channel and/or connected to the guide from the proximal end of the catheter.

Alternatively or additionally, a carriage and/or tool may be introduced into the working channel and/or connected to the guide from the distal end of the catheter.

In some embodiments, a guide may include a track and/or a guide channel. A guide optionally communicates with the working channel and/or the outer surface of the catheter. Optionally a guide and/or guide channel may communicate with the outside of the catheter at its distal and/or proximal end. Optionally, a guide and/or guide channel may communicate with the outside of the catheter along its length. For example the guide may include a narrow guide channel with a longitudinal slit communicating with the working channel and/or the outer surface of the catheter.

Optionally the slit connects to a distal opening and/or to a proximal opening of the guide and/or guide channel and/or working channel. Alternatively or additionally, the slit may run along central and/or interior portion of the guide channel and/or guide.

Optionally a slit runs the entire length of the guide and/or guide channel (for example from a distal end and/or a distal opening to a proximal end and/or a proximal opening). For example, a guide may communicate with the working channel and/or the outside of the catheter along its entire length and/or along a length less than the width of the working channel and/or along a length ranging between the width of the working channel to ten times the width of the working channel and/or along a length ranging between ten times the width of the working channel to one hundred times the width of the working channel and/or over a length less than one tenth the length of the catheter and/or over a length between a tenth to a quarter of the length of the catheter and/or over a length ranging between a quarter to a half the length of the catheter and/or between half the length to the entire length of the catheter. For example, a working channel may communicate with one or more guides and/or the outside of the catheter along its entire length and/or along a length less than the width of the working channel and/or along a length ranging between the width of the working channel to ten times the width of the working channel and/or along a length ranging between ten times the width of the working channel to one hundred times the width of the working channel and/or over a length less than one tenth the length of the catheter and/or over a length between a tenth to a quarter of the length of the catheter and/or over a length ranging between a quarter to a half the length of the catheter and/or over a length ranging between a half to the entire the length of the catheter. The width of a communication slit may range for example between 0.01 to 0.1 mm and/or between 0.1 mm to 0.5 mm and/or between 0.5 mm to 2 mm and/or 2 mm and/or more. The width of a communication slit may range for example between $1/50$ to $1/10$ the width of the smaller channel and/or between $1/10$ to $1/5$ the width of the smaller channel and/or between $1/5$ to $1/2$ the width of the smaller channel and/or from $1/2$ to the entire width of the smaller channel. In some embodiments the width of the slit may be variable along the length of the channel.

In some embodiments, the guide may include a track running along the working channel and/or an outer surface of the catheter. The guide may optionally extend along the entire length of the working channel and/or a portion thereof. The guide may communicate with the working channel along the entire length of the working channel and/or a portion thereof. In some cases a plurality of guides may all have similar width and/or form. Alternatively or additionally, each guide may have a different width and/or form. In some embodiments, a guide may have a cross sectional area ranging between $1/2$ to $1/5$ the cross sectional area of an associated working channel and/or between $1/5$ to $1/20$ the cross sectional area of an associated working channel and/or between $1/20$ to $1/400$ the cross sectional area of an associated working channel.

In some embodiments, a narrow guide channel may be used as a guide and/or used as an alternative working channel. For example, a narrow tool may be introduced into or out of the lumen through a guide channel and/or materials may be passed into or out of the lumen through a guide channel.

In some embodiments a catheter may include and/or not include one or more working channels, internal guides (for example communicating with one or more working channels), external guides (for example communicating with an external surface of the catheter), and/or closed guides. Optionally, a working channel may include a longitudinal opening and/or may be closed. A guide channel may interconnect two channels (for example working channels and/or guide channels) and/or may connect a channel to an external opening.

In some embodiments, a tool deployed on the outside of a catheter may be supplied with shielding. For example a shield may protect internal structures in the patient from damage and/or puncturing by the tool. For example a balloon may be mounted on the tool. Optionally, the tool may be conveyed through the catheter with the balloon in a contracted (for example deflated) state and/or the balloon may be expanded (for example) inflated while the tool is located outside the catheter.

In some embodiments, a working channel is used for transporting tools and/or materials to and/or from the lumen. For example the working channel may include the access path. Alternatively or additionally, the working channel may be included in a catheter. For example, the catheter may be positioned along an access path to the lumen. A guide may be used, for example, to convey one or more tools to the lumen and/or to control the one or more tools in the lumen (for example controlling a tool may include manipulating and/or supporting and/or directing the tool). For example, the tool may be deployed and/or retrieved and/or conveyed through the working channel via the guide. Alternatively or additionally, the tool may be controlled in the lumen via the guide. For example, a tool may be deployed in a lumen connected to a distal end of a guide. Alternatively or additionally, a tool may be directed along a guide to a location in the lumen where the tool can be supported (permanently or temporarily) by a connection to a body part. For example, the tool may remain connected to the guide and/or the tool may be disconnected from the guide. In some embodiments a tool may be deployed inside the lumen such that an opening of the working channel remains clear. Optionally clearing the opening of the working channel may facilitate use of the working channel to pass further tools and/or materials into and/or out of the lumen. Optionally, the tool may be reconnected to the guide and/or the tool may be returned to the working channel and/or retrieved from the lumen through the working channel. Optionally returning and/or retrieving the tool may include directing the tool via a guide to the working channel and/or conveying the tool along the working channel via the guide. Optionally the tool is returned along the same guide that was used to deploy the tool. Alternatively or additionally, the tool may be returned using a different guide. In some embodiments of the current invention, one or more tools may be inserted into a working channel and/or conveyed in a working channel and/or deployed from a working channel and/or retrieved from a working channel without the use of a guide.

In some embodiments the guide may used to convey and/or guide a tool all the way and/or part of the way to a lumen and/or site of treatment. Alternatively or additionally, a tool may arrive to the site of treatment without the guide and/or the guide may be used to retrieve the tool. Alternatively or additionally, a tool may arrive to the site of treatment without the guide and/or the guide may be used to control the tool at the site of treatment.

In some embodiments, a working channel may include a narrowing at one or more locations. In some embodiments, the lumen may include a portion of the urinary tract, the digestive tract and/or the pulmonary tract.

In some embodiments a plurality of guides may be used to control a plurality of tools. For example a plurality of guides may be positioned along the access channel and/or a respective tool connected to each guide. Optionally, each tool is conveyed and/or directed and/or manipulated and/or supported independently.

In some embodiments, a single guide may be used for multiple tools. For example, a first tool may be disconnected from the guide and/of subsequently a second tool may be connected to the guide. For example the first tool may be deployed into the lumen and/or disconnected from the guide. Subsequently, the second tool may be connected to the guide. Alternatively or additionally, the first tool may be returned from the lumen and/or retrieved from the working channel and/or disconnected from the guide. Subsequently the guide is optionally used for a second tool. Alternatively or additionally multiple tools may be connected to a single guide and/or a single tool may be connected to multiple guides.

In some embodiments a tool may block a channel and/or a path. Optionally the tool may be moved to unblock the path and/or channel. For the sake of the current disclosure, unless stated otherwise blocking a path and/or channel is relative to a context. For example, in the context of passing a sequence of tools through a channel, a first tool blocks a channel when the second tool is prevented from passing through the channel due to the first tool. Unblocking the channel may mean allowing the second tool to pass through the channel. Alternatively or additionally blocking may mean preventing a object from passing along the path when the cross sectional area ranges for example between 10% to 25% of the cross sectional area of the channel and/or path and/or 25% to 50% of the cross sectional area of the channel and/or path and/or 50% to 75% of the cross sectional area of the channel and/or path and/or 75% to 100% of the cross sectional area of the channel and/or path. Optionally for the sake of this disclosure unblocking a path and/or channel may mean opening 10 to 25% of the blocked cross section of the path and/or channel and/or opening 25 to 50% of the blocked cross section and/or opening 75 to 100% of the blocked cross section.

In some embodiments, a tool may be inserted into a catheter and/or retrieved from the catheter and/or reinserted into the catheter while the distal end of the catheter remains in a lumen of a patient. For example inserting, retrieving and/or reinserting may be used to reposition a tool and/or a camera in a lumen. For example a camera may be relocated to a new position for example with an improved view and/or a tool may be placed in a new position for example with better access to a treatment location.

In some embodiments of the present invention multiple tools may be retrieved through a narrow working channel. Optionally a working channel may include the working channel of a catheter which is positioned along the path to a treatment site. In some embodiments, one or more tools are optionally passed sequentially through the working channel into the lumen of a patient. In some embodiments, one or more guides may be used to convey one or more tools through the working channel and/or to unblock the working channel. Optionally one tool may be passed into the working channel after the previous tool has passed out of the working channel. Alternatively or additionally, multiple tools may be passed through the working channel in a line. For example, all of the tools may be attached to a single guide. Alternatively or additionally, one or more guides may be used to convey each of a plurality of tools independently through the working channel. For example, the working channel may be too narrow for two tools to pass simultaneously. Optionally, a first tool may be directed along a guide from a location in the working channel to a site outside the working channel unblocking the working channel. Subsequently, the unblocked working channel may be used for another function. For example the unblocked working channel may be used for transporting a fluid into or out of the lumen. Alternatively or additionally, a second tool may be passed along a second guide through the unblocked working channel and/or past the location vacated by the first tool.

In some embodiments, the guide may be used to return a tool from the lumen to outside the lumen, for example to the working channel and/or to return the tool to outside the body of the living creature. For example, a tool may be deployed into a lumen and/or later returned to the working channel and/or retrieved. The tool optionally will remain connected to the guide while it is deployed. Alternatively, the tool may be disconnected from the guide while it is deployed and/or reconnected to the guide when it is returned. For example, a tool may be connected to a tether for return and/or retrieval. Optionally the tool may be deployed returned and/or retrieved along a single guide. Alternatively or additionally multiple guides may be used for conveying, deploying, returning and/or retrieving a tool. For example, multiple guides may be used sequentially and/or simultaneously.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways. Similar steps and/or components and/or aspects may be labeled with the same numbering in multiple Figs. Descriptions of options, components, steps and/or aspects with regard to one Fig. apply also to similarly labeled options, components, steps and/or aspects of other Figs.

Exemplary Embodiments

Method of Opening a Workspace

FIG. 1 is a flow chart illustration of a method for opening a workspace inside a lumen of a living creature in accordance with an embodiment of the present invention.

Optionally access to the inside of the lumen is through a catheter having a distal opening inserted into the lumen. A first anchor may be deployed 101. For example, deployment 101 may include reversibly securing and/or affixing the anchor to a wall of the lumen. The first anchor is optionally deployed 101 proximal to the workspace. A second anchor may be deployed 101 distal to the workspace. Optionally the distal opening of the catheter may be within the work area. The distance between the anchors may be expanded 105 thereby stretching the lumen longitudinally.

Longitudinal stretching optionally straightens folds in the walls of a lumen.

Unfolding may for example expose parts of the wall and/or other structures that were obscured by the folds. Once the structures are exposed a medical procedure (for example a diagnostic and/or therapeutic procedure) may be performed 107.

The anchors may optionally be used to laterally expand the lumen and/or to seal the working area. For example, sealing the working area may be used to prevent the transfer of dirt and/or body fluids into the workspace and/or to prevent transfer of drugs, medical materials and/or debris out of the workspace. Sealing may also facilitate inflation of the workspace.

Once diagnostic and/or therapeutic procedures have been completed, the lumen is optionally released from its stretched configuration and/or tools and/or anchors and/or the catheter may be released and/or returned 111.

System for Opening a Workspace

FIGS. 2A-3B illustrate a tool, for example a dissector, for opening a workspace in a lumen of a living creature in accordance with an embodiment of the present invention.

Optionally, the tool may include a first anchor located proximal to a distal opening of a catheter. Additionally or alternatively, the tool may include a second anchor that can be moved distally with respect to the distal opening. For example the second anchor may be mounted on an extender, for example shaft that moves through and/or out the distal opening. The anchors are optionally secured to the walls of the lumen and then distanced one from the other to longitudinally stretch and/or unfold the lumen.

Figure 2A:
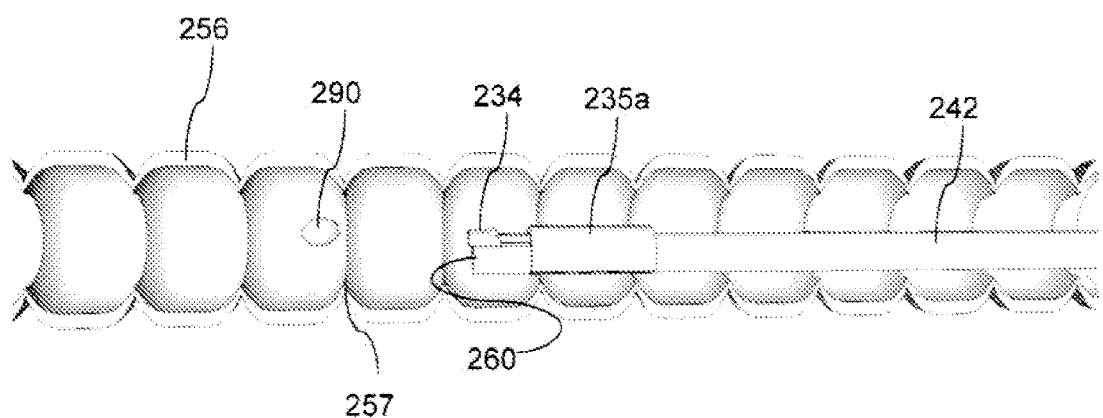
FIGS. 2A-D illustrate deploying of a system for opening a workspace in a lumen in accordance with an embodiment of the present invention.

FIG. 2A is a cut away view of a folded lumen 256 containing a dissector catheter 242 in accordance with an embodiment of the current invention. Catheter 242 optionally includes a distal opening 260 inserted into folded lumen 256. For example, catheter 242 includes an anchor 235a in a contracted state wrapped around a sleeve of catheter 242. For example, anchor 235a may be located proximal to distal opening 260 of the catheter.

In some embodiments, lumen 256 may include an intestine. A structure 290 of interest may be partially obstructed by a fold 257 in lumen 256. For example, structure 290 may include a polyp.

Figure 2B:
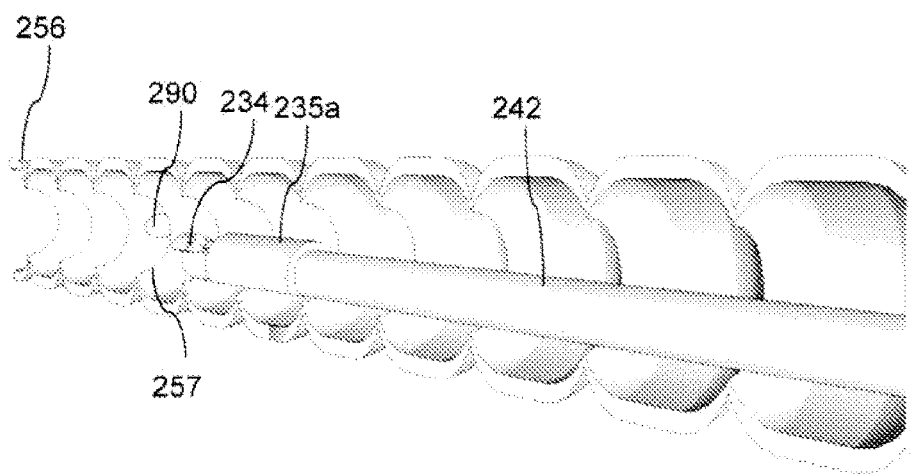

FIG. 2B illustrates a cutaway perspective view of lumen 256 including catheter 242 in accordance with an embodiment of the present invention. In the exemplary view, structure 290 is viewed from the perspective of an imaging sensor 234 looking distally from the distal end of catheter 242. Structure 290 may be partially and/or totally obstructed by a fold 257 in lumen 256. For example, in FIG. 2B, only a top portion of structure 290 is within the view of imaging sensor 234.

Figure 2C:
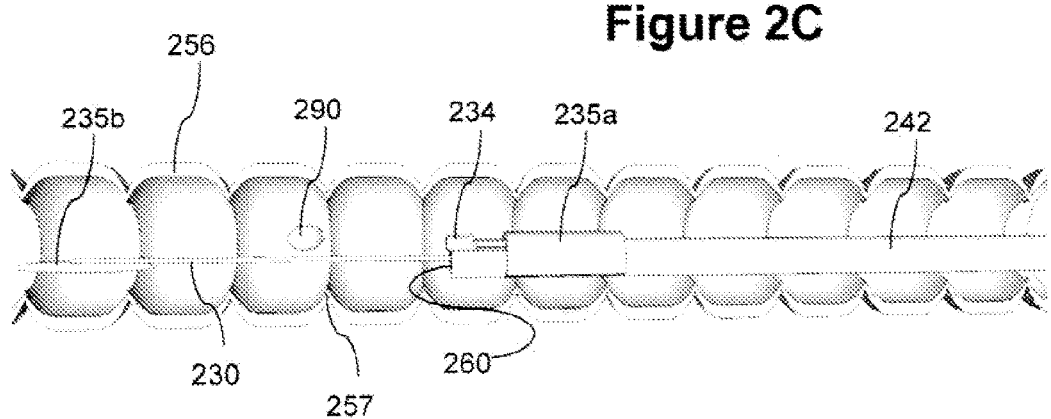
Figure 2D:
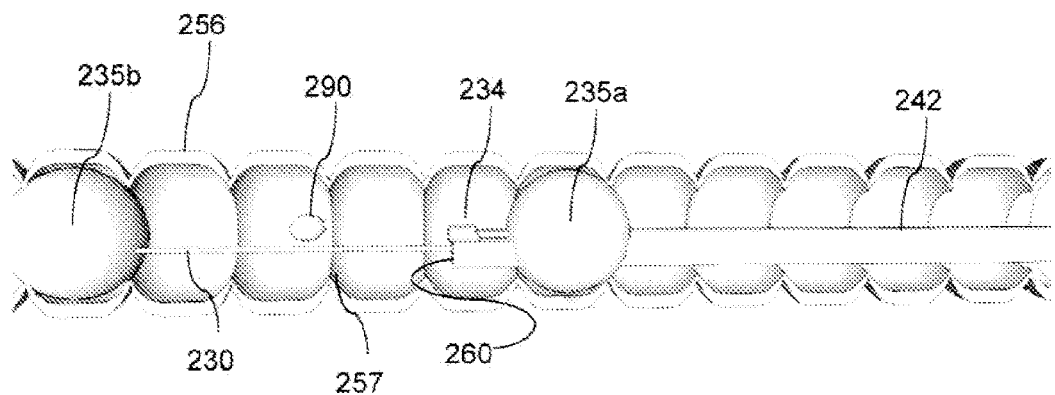

FIGS. 2C and 2D illustrate deployment of two anchors 235a, b from catheter 242 inside lumen 256 in accordance with an embodiment of the current invention.

Optionally, catheter 242 is located in lumen 256 with distal opening 260 of the catheter proximal to structure 290. A first anchor 235a is optionally located on one side (proximal to) structure 290. A second anchor 235b is inserted through catheter 242 and/or through distal opening 260 into lumen 256. Optionally, anchors are located on two sides of a fold is in lumen 256. For example, anchors 235a, b are located on opposite sides of fold 257. Optionally, when inserted, anchor 235b is in a collapsed state, as illustrated for example in FIG. 2C. Anchor 235b is optionally inserted longitudinally along lumen 256 past structure 290. For example, as illustrated in FIG. 2C, anchor 235b is placed on the distal side of structure 290 opposite anchor 235a.

In some embodiments, once an anchor is in place, it is reversibly affixed and/or secured to a wall of the lumen. For example, anchors 235a, b may include one or more balloons. Once anchors 235a, b are positioned on opposite sides of structure 290, the balloons are optionally inflated (for example as illustrated in FIG. 2D). Inflation may secure the anchor to the lumen for example by being pressed against the wall of the lumen. Alternatively or additionally an anchor may be secured to a lumen wall by suction. For example an anchor may include an opening in communication with a vacuum source. The opening may optionally be placed near the wall of the lumen and suction applied to affix the anchor to the wall. In some embodiments, inflating a balloon in lumen 256 may have an effect of opening the workspace laterally and/or of sealing off the workspace.

Figure 3A:
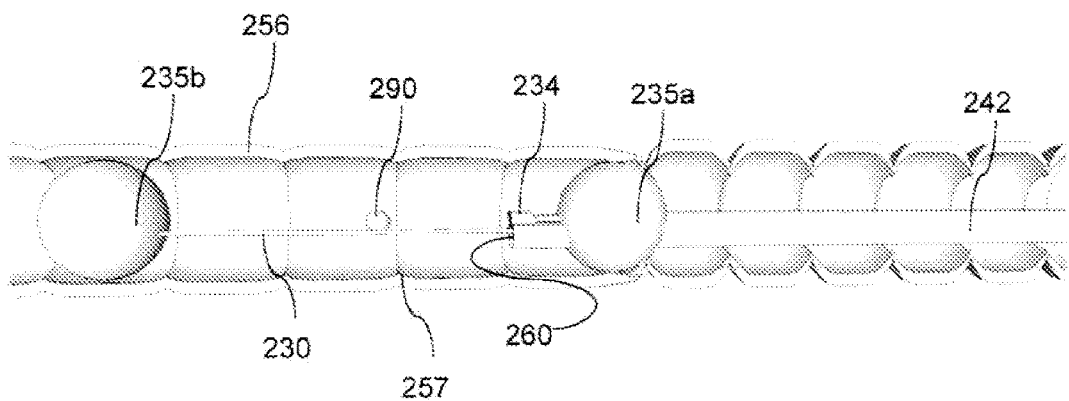
FIGS. 3A-B illustrate opening a workspace in a lumen in accordance with an embodiment of the present invention.
Figure 3B:
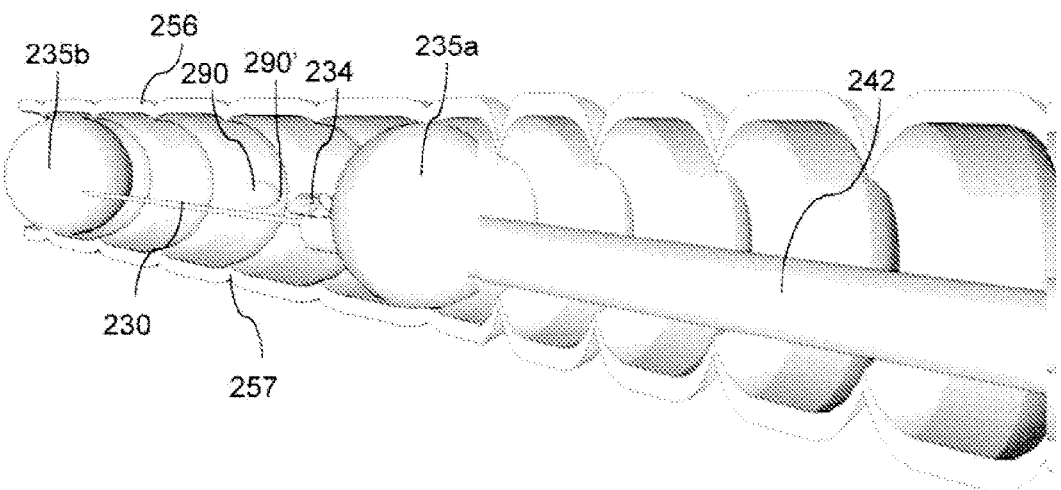

FIGS. 3A and 3B illustrated a workspace in an opened state in accordance with an embodiment of the current invention. In some embodiments once anchors 235a, b have been affixed to the walls of lumen 256 on opposite sides of structure 290 and/or on opposite sides of fold 257, the distance between anchors 235a, b may be expanded.

In some embodiments, expanding a distance between the anchors may include advancing an extender, for example a carriage 230, distally from the distal opening of the catheter. For example, carriage 230 may include a shaft extending along a channel and/or a guide of catheter 242. For example, the shaft may be inserted from a proximal opening of catheter 242 to distal opening 260 and/or out distal opening 260 into lumen 256. Optionally a guide may support the anchor and/or extender at a fixed point at the distal opening of the catheter.

In some embodiments, expanding distance between anchors 235a, b optionally stretches lumen 256 longitudinally and/or opens folds between anchors 235a, b. For example, anchors 235a, b may be located on opposite sides of fold 257. For example, a line joining the locations of anchors 235a, b may be perpendicular to the line of fold 257.

Optionally as seen in FIGS. 3A-B, the workspace between anchors 235a, b is opened by lateral expansion caused by inflation of the balloons. Alternatively or additionally, as illustrated in FIGS. 3A-B, the workspace between anchors 235a, b is opened by stretching longitudinally and/or opening folds 257 by expanding the longitudinal distance between anchors 235a, b. Opening folds optionally exposes a previously obscured structure. For example as illustrated in FIG. 3B, longitudinally expanding the workspace unfolds fold 257 in lumen 256 and/or exposes the root 290' of the polyp (structure 290) to inspection and/or treatment. For example, with the workspace in an unfolded state structure 290 can be cut off at its root 290'. Optionally, expanding the distance between anchors 235a, b is by extending carriage 230 out from distal opening 260. Alternatively or additionally an extender may be expandable. For example an extender may include a spring that is held in a compressed state and released to expand a distance between anchors. Alternatively or additionally, an extender may have a limp and/or a stiff configuration. For example the anchors may be affixed to the lumen with the extender in a limp state and then the extender may be stiffened, expanding the space between the balloons. For example, an extender may be stiffed by inflation, for example by fluid pressure and/or an extender may include a nitinol part that changes properties. Alternatively or additionally, an extender may include interlocking parts that are pulled together to stiffen the extender and/or to expand the distance between the anchors. For example there may be a control mechanism for stiffening the shaft. Optionally the control mechanism is accessible from outside a proximal opening of a catheter. For example, the stiffening control mechanism may include a syringe for increasing pressure in an extender and/or a drawstring to pull together and/or stiffen a set of links that are flexible when they are loose and become stiff when pulled together and/or an stiffening control may include a release for a spring and/or a mechanism for compressing a spring. Optionally a stiff extender may resist buckling and/or compression. For example, a stiff extender may retain between 30% to 60% of its length under compression and/or between 60% to 80% of its length and/or between 80% to 90% of its length and/or between 90% to 95% of its length and/or between 95% to 98% of its length and/or between 98% to 100% of its length under a compression force of for example between 0.01 and 0.1 Newton's and/or between 0.1 and 0.5 Newton's and/or between 0.5 and 1 Newton's and between 1 and 5 Newton's.

In some embodiments, the distance between anchors 235a,b may range for example between 2 to 15 cm. Optionally, when distance anchors 235a,b is expanded it may be extended between for example 1 to 5% and/or 5 to 30% and/or 30 to 70% and/or 70% to 120% and/or 120% to 200%. Optionally the distance will be expanded until a fold is sufficiently opened to access an object. For example the system may include a sensor to sense the opening of a fold and/or a controller responsive to the sensor to continue distancing the anchors until the fold is sufficiently open and/or stop distancing the anchors when the fold is sufficiently open.

In some embodiments, conveyance of anchor 235b and/or tools and/or fluids to lumen 256 may be through a working channel of catheter 242 and/or with the assistance of one or more guide channels, for example as explained herein below with regards to FIGS. 6A-D. Optionally, while anchor 235b is deployed in lumen 256, carriage 230 may be supported by the guide. For example, anchor 235b may be inserted into catheter 242 through a proximal opening of catheter 242 and/or may be conveyed through the catheter to distal opening 260. For example, catheter 242 may include one or more guide channels communicating with the working channel. For example, as illustrated in FIGS. 6A-D, carriage 230 may be supported and/or directed by the guide channel. Optionally, tools and/or fluids may be transported into and/or out of the working space through the catheter while anchors 235a, b are in deployed and/or while the workspace is open.

In some embodiments an anchor may be released (for example by deflation) and/or retrieved from the lumen and/or may be replaced by a different tool and/or anchor. For example, an anchor may be drawn back from the lumen into the distal opening of the catheter and/or conveyed along the catheter to the proximal opening and/or drawn out of the proximal opening. For example, an anchor may be replaced by a larger anchor (that may, for example, be inserted from the proximal opening of the catheter to the distal opening and/or the lumen). For example, a balloon may be used to expand a lumen and then replaced with another balloon as the lumen stretches.

Progressively expanding the lumen with larger and larger balloons may be used to open a stricture in the lumen.

Figure 4A:
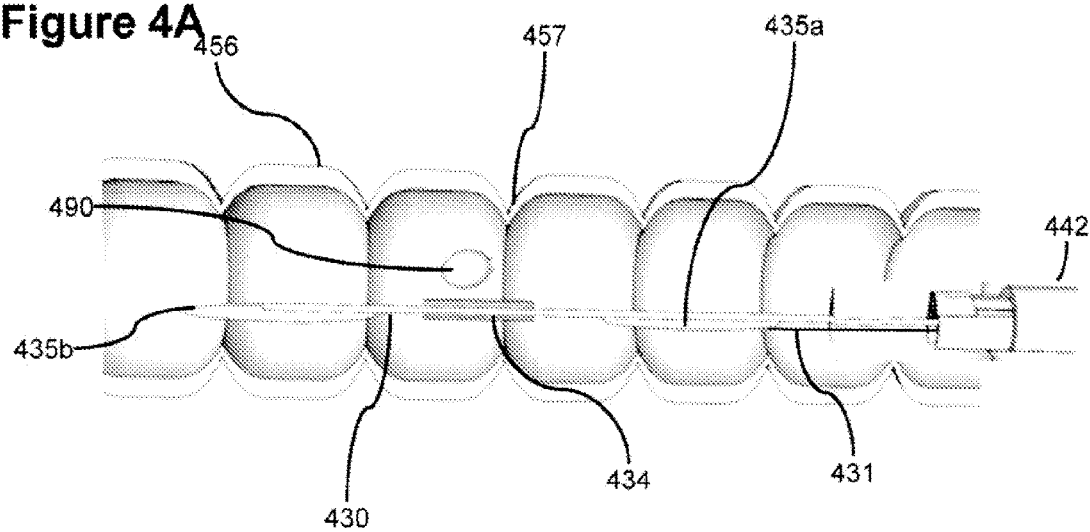
FIGS. 4A-C are a schematic illustration of opening a workspace in a lumen in accordance with an embodiment of the present invention.
Figure 4B:
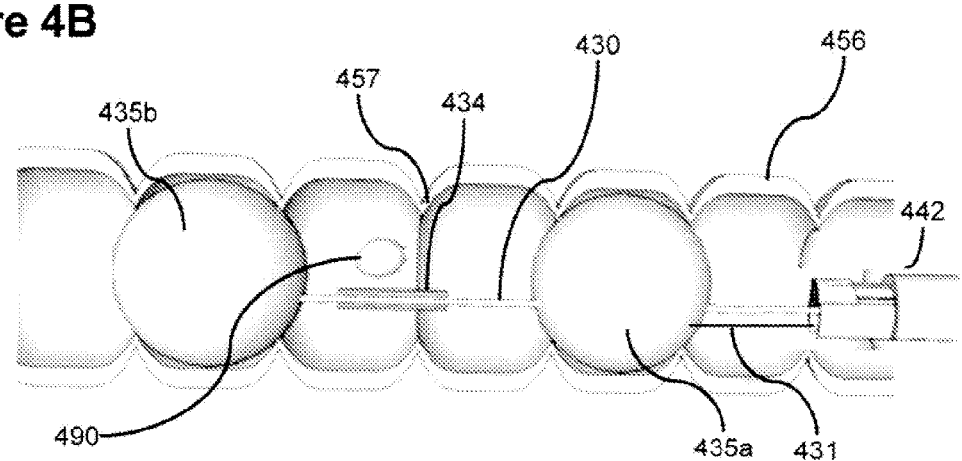
Figure 4C:
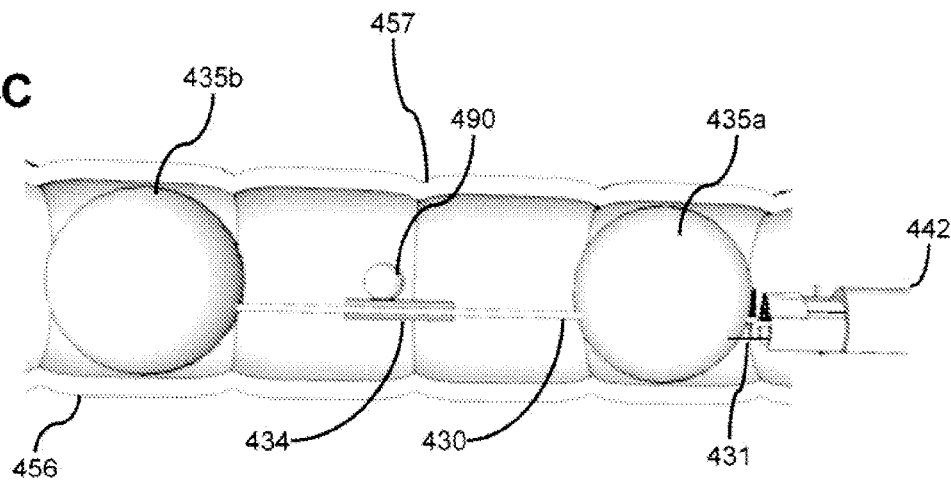

FIGS. 4A-C illustrate an alternative embodiment of a system for opening a workspace. Optionally, a system for opening a workspace includes one or more anchors and/or a tool that can be inserted into a lumen through a catheter.

FIG. 4A illustrates insertion of a system for opening a workspace into a lumen in accordance with an embodiment of the current invention. In some embodiments, two anchors 435a, b may be mounted on a shaft 430 on either side of a tool 434. The system may be inserted through a catheter into a lumen 456 near a structure 490 and/or a region of interest. Optionally, the system is inserted through catheter 442 in a collapsed state.

FIG. 4B illustrates deployment of a system for opening a workspace in accordance with an embodiment of the present invention. Anchors 435a, b may include for example Nitinol rings that expand to affix by friction and/or by pressing themselves onto the pliable walls of the lumen. Alternatively or additionally an anchor may include a friction attachment and/or a vacuum attachment and/or another attachment means.

FIG. 4C illustrates a system to open a workspace longitudinally expanding a workspace in accordance with an embodiment of the present invention. Optionally, after affixing anchors 435a, b to the walls of lumen 456, the longitudinal distance between anchors 435a, b is expanded. For example, a cord 431 may be attached to anchor 435a. An operator outside a proximal opening of catheter 442 may hold shaft 430 steady while pulling cord 431. Pulling cord 431 optionally slides anchor 435a proximally along shaft 430 while holding shaft 430 steady keeps anchor 435b fixed in relation to catheter 442. As anchor 435a slides proximally, the longitudinal distance between anchors 435a and 435b is optionally increased, stretching and/or unfolding lumen 456 in the workspace between anchors 435a,b. In particular, in the embodiment of FIGS. 4A-C, opening fold 457 exposes structure 490 to diagnosis and/or treatment using tool 434. In some embodiments, tool 434 may include for example a sensor, an ablation device (for example a radio frequency electrode), a nozzle for applying a stream of cleaning fluid and/or a suction, a pincer, a cutter, a sample collection bag, and/or a medicine application device (for example a microneedle). In some embodiments, anchors 435a, b may seal off the workspace. For example a medicine and/or a dye may be injected into the sealed workspace for further diagnostic and/or treatment regimes.

Tool for Use with a Multi-Channel Catheter

Figure 5A:
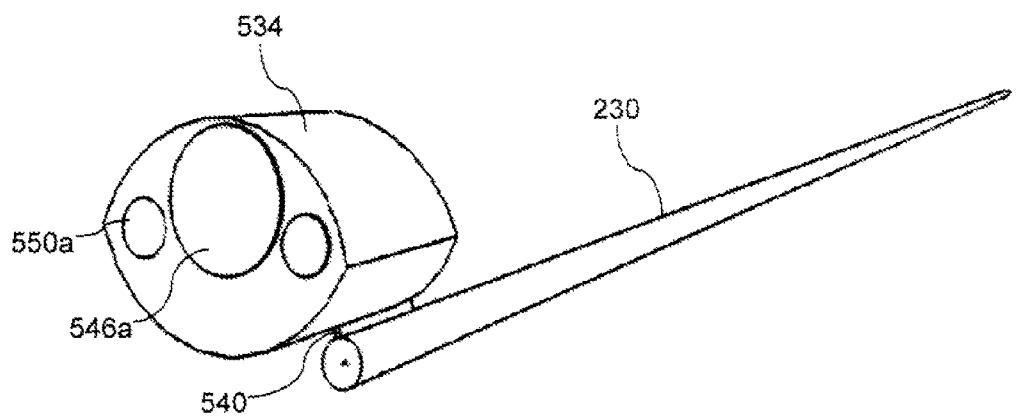
FIGS. 5A-B are perspective views of a tool on a carriage in accordance with an embodiment of the present invention.
Figure 5B:
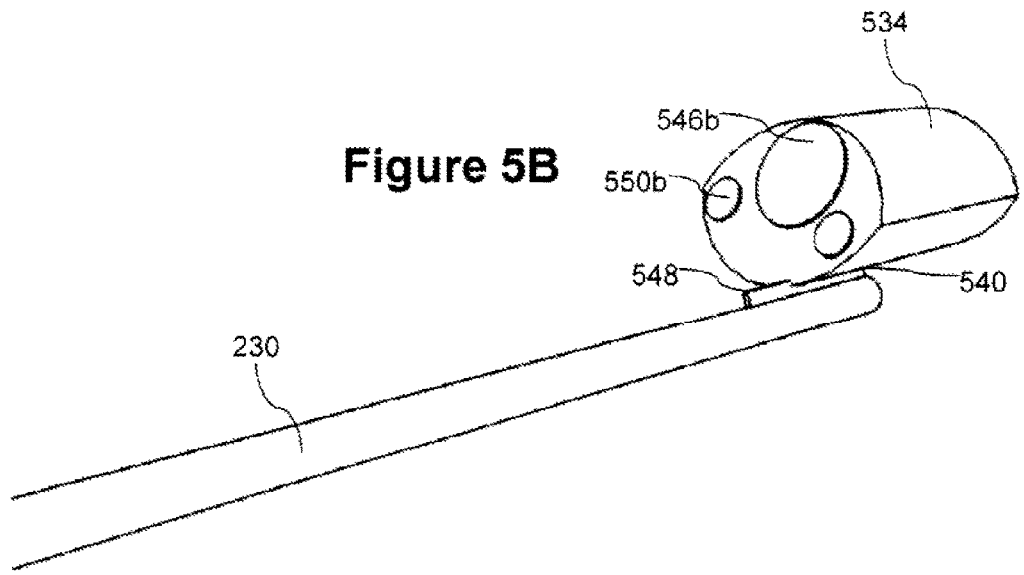

FIGS. 5A and 5B illustrate two perspective views of a tool 534 for use in a lumen of a patient in accordance with some embodiments of the present invention. For example tool 534 may include one or more cameras 546a, b and/or one or more light sources 550a, b. Alternatively or additionally tool 534 may include an anchor (for example anchor 235a and/or 235b). Tool 534 is optionally mounted on a carriage 230.

Optionally carriage 230 may connect to a guide. For example, a guide may direct and/or convey and/or stabilize carriage 230 and/or tool 534 inside a working channel and/or inside a lumen, for example as explained herein below.

In some embodiments, carriage 230 may include a flexible and/or elastic rod and/or wire. For example, carriage 230 may be used to push and/or pull tool 534 along an access pathway (for example a working channel) to a lumen. Alternatively carriage 230 may be used to support and/or manipulate tool 534 in the lumen. Carriage 230 is optionally flexible enough to follow curves in the working channel, but stiff enough to retain its length (for example without folding over and/or significantly stretching). In some embodiments a carriage may be torsion resistant. For example, a user may twist a proximal end of the carriage 230 in order to rotate the tool 534 around the axis of carriage 230.

In some embodiments, tool 534 may be joined to carriage 230 by a mount 540.

Carriage 230 and/or tool 534 may include an orientor 548. For example, orientor 548 may orient and/or stabilize tool 534 with respect to a guide and/or with respect to a catheter and/or with respect to another tool (for example as illustrated in FIGS. 6A-F).

In some embodiments, tool 534 is permanently connected to mount 540 and/or carriage 230. Alternatively or additionally, a mount may be reversibly connected to the tool. For example the tool may be connected and/or disconnected and/or reconnected to the carriage and/or guide and/or a manipulator. Optionally, tool 534 is directly and/or physically attached to carriage 230 and/or mount 540. Optionally or additionally, a tool may be connected to a carriage by a magnet or other indirect method.

Inserting a Tool into a Catheter with Guides

FIGS. 6A-F illustrate insertion and deployment of a tool with a catheter in accordance with an embodiment of the current invention. Optionally, a catheter includes an outer sleeve 642. Outer sleeve 642 optionally includes one or more large working channels 628. In some embodiments sleeve 642 includes one or more guides 632 and/or 632'. For example, guides 632 may include narrow guide channels.

Optionally guides 632, 632' may be oriented parallel to working channel 628.

Optionally guides 632 and/or 632' may communicate with working channel 628 and/or with a region on the outside of the catheter. For example guides 632 and/or 632' may convey carriage 230 and/or tool 534 along working channel 628 and/or outside the catheter. Optionally, outer sleeve 642 includes a mount 640. For example, mount 640 may be used to steady and/or support a tool, for example tool 534.

In some embodiments, one or more of guides 632 and 632' may be distributed around working channel 628. Optionally, a guide 632 runs the entire length of working channel 628. Alternatively or additionally, guide 632 may run along a portion of the length of the working channel 628. Optionally, a guide 632 communicates with working channel 628 and/or the outside of the catheter along its entire length and/or along a portion of its length.

In some embodiments, a guide 632 may include a guide channel. For example a guide channel may be narrower than the working channel 628. Communication between guide 632 and working channel 628 is optionally supplied by a longitudinally communication opening 636 for example in the form of a slit between guide 632 and working channel 628.

In some embodiments, a guide 632 and/or a working channel 628 may communicate with a space outside the catheter. Optionally a guide or guide channel and/or a working channel may communication with the outside of the catheter at one or both of the distal and/or proximal ends. For example a guide channel (for example guide 632) may include a distal opening 658 and/or a proximal opening. For example working channel 628 may include a distal opening 660 and/or a proximal opening (for example see proximal opening 661 of FIG. 6B). Alternatively or additionally, one or both ends of a guide channel and/or working channel may be closed.

In some embodiments, a guide and/or a working channel may communicate with the space outside the catheter along all or part of its length. For example guide 632' communicates with the outside of the catheter along a portion of its length via a communication opening 636'. For example guides 632 and 632' communicate with the working channel 628 along their entire length via openings 636. Optionally openings 636 connect to distal openings 658 at the distal ends of respective guides 632 and 632'.

Optionally, working channel 628 communicates with the exterior of the catheter along its length via a slit, for example longitudinal opening 644. For example longitudinal opening 644 may allow movement of large objects along working channel (for example while a portion of the object protrudes out of opening 644). For example longitudinal opening 644 may facilitate insertion of outer sleeve 642 around an endoprobe and/or longitudinal opening 644 may facilitate conveyance of a large object.

Figure 6A:
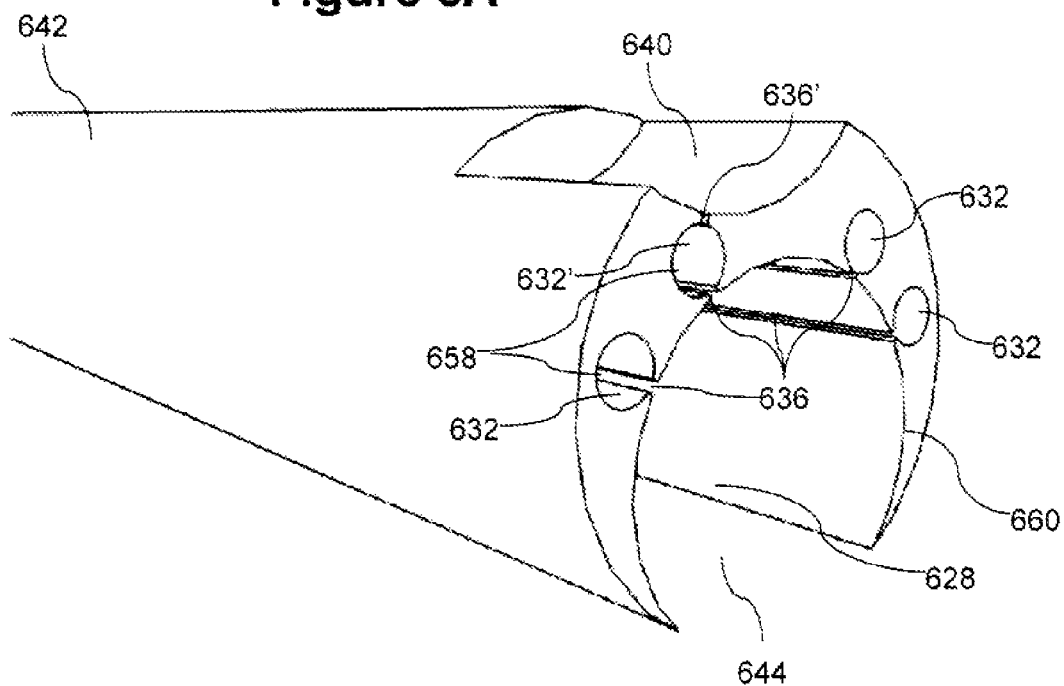
FIGS. 6A-F are perspective views of various stages of deploying a tool on a carriage with a multi-channel catheter in accordance with an embodiment of the present invention.
Figure 6B:
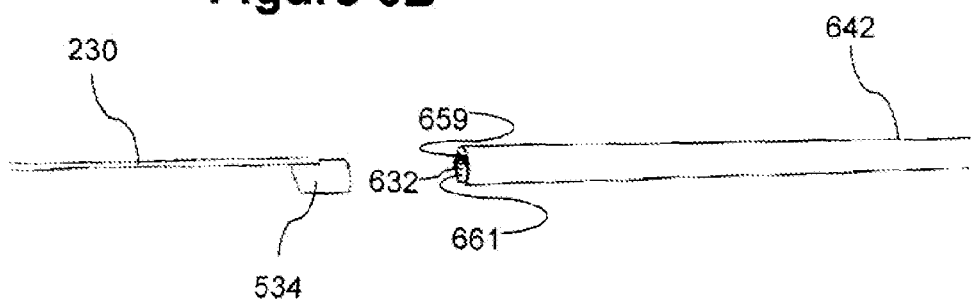
Figure 6C:
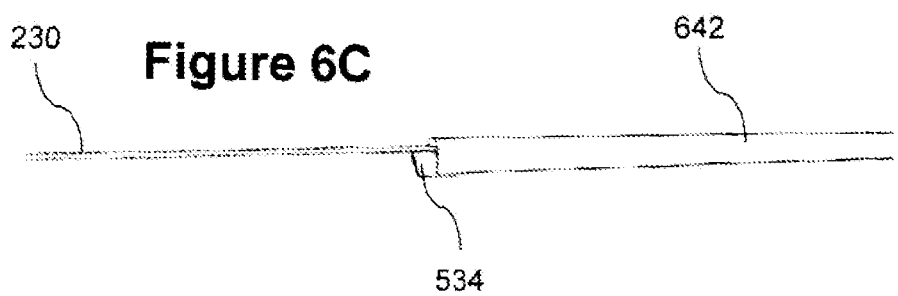
Figure 6D:
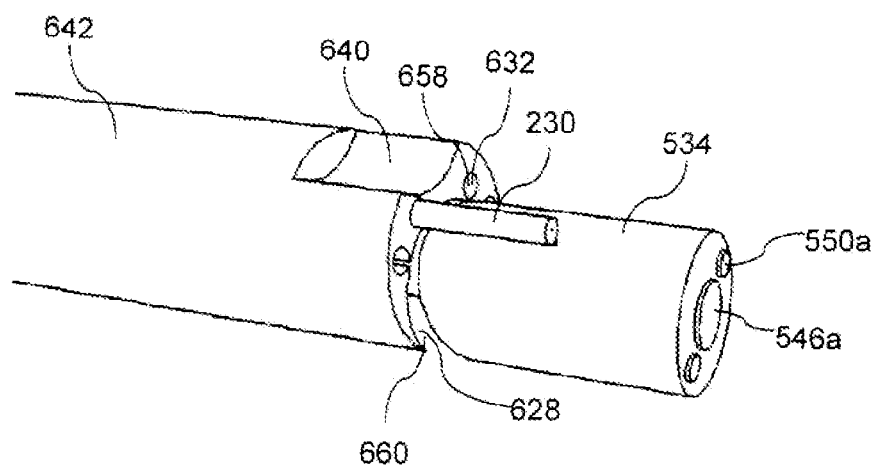
Figure 6E:
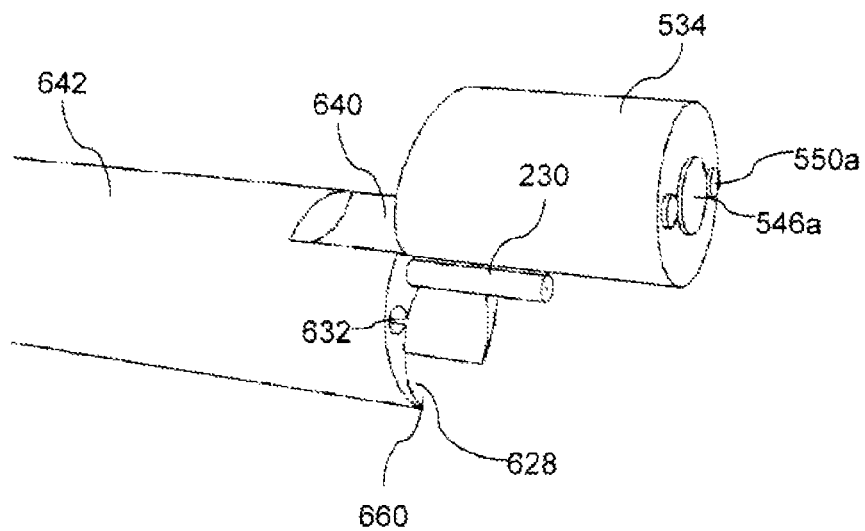
Figure 6F:
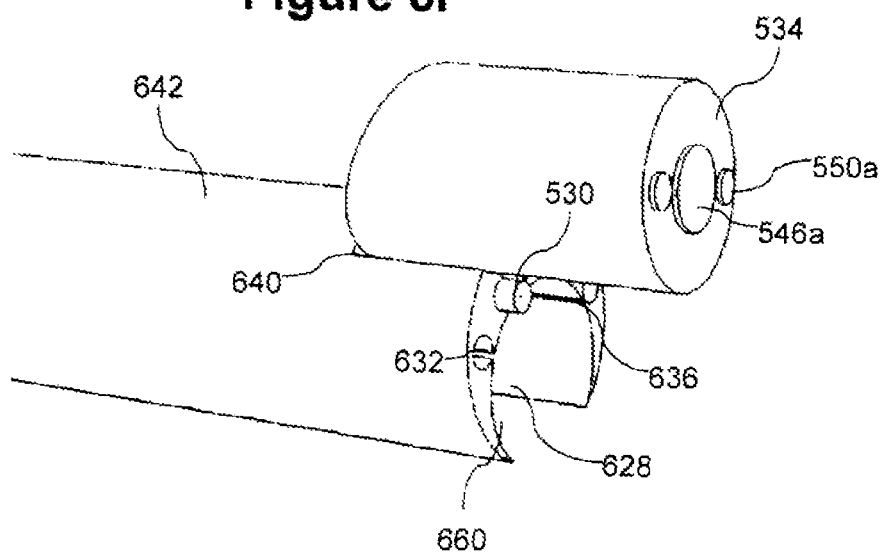

FIGS. 6B and 6C illustrate insertion of a tool into a catheter in accordance with an embodiment of the current invention. For example tool 534 is inserted into proximal opening 661 of outer sleeve 642. Optionally, carriage 230 is inserted into guide 632'. Optionally mount 540 passes through opening 636' connecting tool 534 to carriage 230. Alternatively or additionally, a guide may be closed (without a slit) and/or a carriage passing through the guide may be connected to the tool via a magnet and/or another means.

In some embodiments a guide and/or carriage may be used to manipulate and/or convey a tool inside a working channel. For example, carriage 230 may be used to push and/or convey tool 534 through working channel 628. For example, in FIGS. 6C and 6D, carriage 230 has been pushed from proximal opening 659 through guide 632' until carriage 230 reaches and/or extends out of distal opening 658. Optionally carriage 230 pushes tool 534 through working channel 628 from proximal opening 661 until it reaches and/or extends out of distal opening 660.

In some embodiments, a carriage and/or guide may be used to deploy and/or steady and/or support a tool outside of a catheter. For example in FIG. 6C tool 534 and/or a distal end of carriage 230 and/or mount 540 and/or orientor 548 have been extended and/or deployed out distal openings 658 and 660 of guide 632' and/or opening 636 and/or channel 628 respectively. Optionally, a clearance is provided between tool 534 and the distal end of the catheter. Optionally a center portion of carriage 230 remains inside guide 632' and/or a proximal portion of carriage 230 extends out proximal opening of guide 632'.

In some embodiments, a carriage and/or guide may be used to manipulate a tool outside of a catheter. For example, after extending carriage 230 and/or tool 534 out of the distal end of the catheter, one/or both may be rotated into the configuration of FIG. 6E and/or retracted to the configuration of FIG. 6F. A user (for example a doctor performing a medical procedure with the catheter), may optionally twist the proximal end of carriage 230. For example, twisting carriage 230 while it is supported inside guide 632' and/or while the distal end of carriage 230 and/or tool 534 are extended out of working channel 628 may move tool 534 away from the axis of working channel 628. Optionally, working channel 628 is unblocked and/or can be used for a further function. In the deployed position of FIG. 6F, the lenses of tool 534 are above the axis of sleeve 642. For example, this allows a camera in tool 534 to see backward without being blocked by sleeve 642.

In some embodiments, a tool may be supported and/or steadied on an outside surface of a catheter. For example, in FIG. 6F, carriage 230 is used to pull tool 534 onto mount 640. Optionally, the distal end of carriage 230 is retracted at least partially back into guide 632' (for example by a user pulling on the proximal end of carriage 230). Optionally, tool 534 is pulled back onto mount 640. Optionally, mount 540 and/or orientor 548 are pulled into slit communication opening 636' orienting, supporting and/or steadying tool 534 on the outer surface of outer sleeve 642.

Optionally, carriage 230 remains inside of guide 532' retaining tool 534 in place on mount 540. Optionally, subsequently carriage 230 may be used to push tool 534 back off of mount 540 and/or to return tool 534 back into working channel 628 and/or to retrieve tool 534 out proximal opening 661 of working channel 628.

Optionally, while tool 534 is steadied on mount 640, carriage 230 may be disconnected and/or retracted out of guide 532'. Optionally, while tool 534 is steadied on mount 640, carriage 230 may be reconnected to tool 534 for example to return tool 534 to working channel 628.

In some embodiments, outer sleeve 642 may be inserted to a location in the subject and then tool 534 may be inserted using working channel 628 as an access channel. Alternatively or additionally, tool 534 may be positioned at the distal end of sleeve 642 before inserting sleeve 642 into a subject. Alternatively or additionally, a distal end of sleeve 642 may be inserted partially into the subject (for example past a narrowing of the access path) and then tool 534 may be positioned at the distal end of sleeve 642.

Application of a Multi-Function Catheter

Figure 7C:
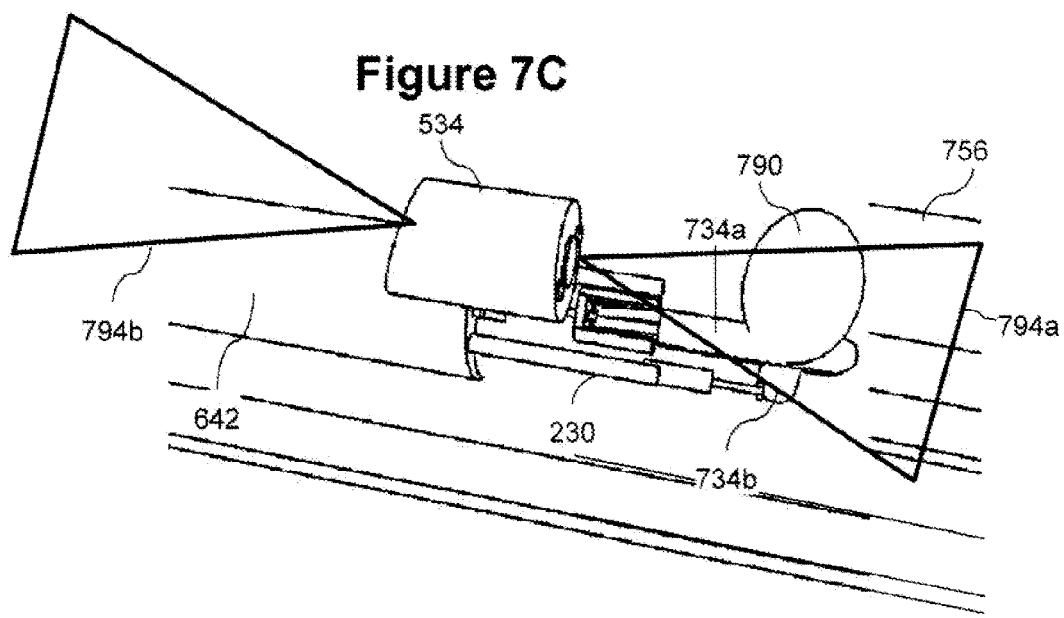

FIGS. 7A-C are perspective views of a catheter in use for removing a growth (example a polyp) in accordance with an embodiment of the current invention. In the example various tools are applied over time to detect a health condition and/or intervene with a treatment.

FIG. 7A illustrates a multi-function catheter in a search mode in accordance with some embodiments of the current invention. For example, the search mode may be used for detection of a disease within a lumen 756 (for example an intestine).

Optionally, tool 534 includes a camera and/or is mounted on a catheter sleeve 642. Tool 534 is mounted off the axis of the catheter with a field of vision 794a distal to the catheter (looking forward) and a field of vision 794b looking backward (proximally from the distal end of the catheter). In some embodiments, sleeve 642 may be inserted into the lumen in the configuration of FIG. 7A. Optionally, while the catheter is inserted into the lumen the camera may be used to search for symptoms.

Alternatively or additionally, tool 534 may be positioned coaxially with the catheter (for example as illustrated in FIG. 6C) reducing the profile of the catheter.

Alternatively or additionally, tool 534 may be located in the distal end of working channel looking ahead (out the distal end of the channel) while the catheter is being inserted. Optionally, a guide wire and/or camera may first be placed into lumen 756 and then sleeve 642 may be inserted over the guide wire.

In some embodiments, positioning a tool 534 outside the axis of a catheter (as depicted for example in FIGS. 6F and/or 7A-C) may be useful in searching for symptoms in a lumen. For example, a camera that can see in both directions may allow searching the lumen while inserting the catheter and/or while removing the catheter. A camera with a field of vision 794a, b may allow view both sides of an object (for example as the camera approaches an object the object is viewed from one side with the one field of vision 794a, b and/or after the catheter passes by the object, the other side of the object is seen with the other field of vision 794b, a. For example, a catheter may be inserted beyond a region of interest and then drawn back while searching for a condition requiring treatment. Tool 534 may optionally include a long focal length camera looking backward and/or proximally (for example field of vision 794b). The backwards field of vision 794b may be used for spotting suspicious objects.

Optionally, the forward field of vision 794a may be used for spotting suspicious objects from the opposite side. Depending on the location of abnormal structures, obstructions etc. an object may be more easily spotted from one side. Additionally or alternatively, the trailing field of vision (for example the forward field of vision 794a when searching is performed while removing the catheter and/or the rearward field of vision 794b when searching is being done as the catheter is inserted) may have a smaller focal length than leading field of vision and/or may be used for investing objects closely and/or during an intervention.

In some embodiments, when the distal end of the catheter passes a suspicious object spotted previously in the rear facing field of vision 794b, the forward field of vision 794a may be used for investigating the suspicious object and/or for directing intervention targeting the object. Optionally, a camera used for investing objects and/or directing intervention may have a smaller focal length and/or narrower field of view than a camera used for spotting objects. Alternatively or additionally, once a suspicious object is spotted, further sensors may be deployed for diagnosing the object. For example, the further sensors may include a camera with specific frequency band sensitivity (for example for spectral analysis) and/or having higher resolution and/or a shorter focal length and/or a temperature sensor and/or a chemical sensor etc.

Deployment of further sensors may optionally be made while the catheter and/or the originally camera of tool 534 remains deployed (thus keeping sight of the object and/or avoiding loosing contact with the object while deploying the new sensor).

In some embodiments, for example when an object of interest is obscured by a fold in a lumen, search mode may include opening a workspace, for example as described herein above with respect to FIGS. 1, 2A-D, 3A-B and/or 4A-C. For example, anchor 235*a* may be inserted into the catheter using carriage 230 and/or guide 632' (optionally after a camera and/or associated carriage are removed from guide 632' and/or mount 640). Anchor 235*a* may optionally be supported on mount 640 and inflated, for example as illustrated in FIG. 3A. For example, anchor 235*b* may be inserted into the catheter using carriage 230 and/or guide 632. Anchor 235*a* may optionally be supported on carriage 230 and inflated, for example as illustrated in FIG. 3A.

FIG. 7B illustrates a catheter in a treatment mode in accordance with some embodiments of the current invention. Optionally, a catheter is switched from the search mode to the treatment mode when a condition is found that requires treatment. A catheter may have multiple search and/or treatment modes that may be selected during a medical procedure and/or without removing the catheter from the patient.

Optionally, to change modes, tools are introduced and/or removed and/or replaced while the distal end of the catheter remains in the lumen and/or the treatment site and/or sensors (for example in tool 534) keep track of the object. In the exemplary embodiment of FIG. 7B, a forceps (for example tool 734*a*) and a cutter (for example tool 734*b*) are deployed for an intervention. Optionally, treatment mode may also include opening a workspace. For example, before starting a treatment, the workspace may be opened for example as described herein above with respect to FIGS. 1, 2A-D, 3A-B, 4A-C and/or 7A.

FIG. 7C illustrates an exemplary intervention in accordance with an embodiment of the current invention. For example, a structure 790 (including for example a polyp) may be grasped with forceps (e.g. tool 734*a*) and/or cut off with cutter tool 734*b*. Guides (for example guide 632) and/or carriages (for example carriage 230) are optionally used to control tools 734*a* and/or 734*b* to perform the procedure. Optionally a sample bag may be deployed and/or used to retrieve polyp (e.g. structure 790). When necessary a tool can be retrieved and/or redeployed in a different guide for improved access to a treatment site. In some embodiments, further diagnostic and/or treatment tools may be deployed to while the catheter and/or a sensor remains in place while tracking the suspicious object. After a procedure is completed tools 734*a* and/or 734*b* are optionally retrieved and/or new tools are optionally deployed for a further procedure and/or search mode is restarted. Retrieving and/or deploying tools and/or changing modes are optionally carried out while the distal end of sleeve 642 remains in the lumen and/or the site of the procedure. Optionally after the procedure, a search for suspicious objects is resumed. Optionally, as further objects are identified and/or diagnosed further treatment and/or investigative and/or diagnostic tools may be deployed using the same catheter which optionally remains in the lumen.

Sensor Array

Figure 8:
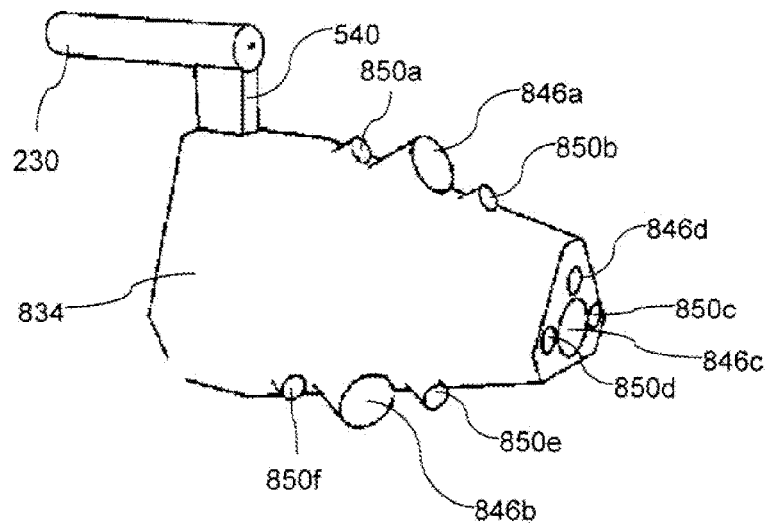
FIG. 8 is a perspective view of an imaging sensor in accordance with an embodiment of the present invention.

FIG. 8 is a perspective illustration of a sensor array in accordance with an embodiment of the present invention. For example sensor array 834 includes imaging sensors 846*a-d* and/or light sources 850*a-f*. Sensor array 834 is optionally mounted on a carriage 230 for deployment and/or manipulation through a working channel and/or in a lumen. For example sensors may be directed forward, backward and/or towards the sides. Different sensors may have different focal lengths, width of field of view, sensitivity, band sensitivity. Light sources 850*a-f* may optionally vary in their intensity, bandwidth and/or focus. Sensor array may optionally be inserted from the proximal opening of a catheter (for example outside a lumen) to a distal opening (for example inside the lumen) and/or deployed away from the axis of a channel. When an interesting object is detected with one sensor, sensor array 834 is optionally moved (for example by rotating around carriage 230 and/or by removing from the catheter and redeploying supported by a different guide and/or by deploying further from and/or closer to the distal opening of the catheter). Optionally, by moving sensor array 834 an operator gets a more detailed view and/or a view in more than one lighting band and/or more than one viewing band. Array 834 may optionally be used to get multiple views and/or multiple spectral images. The multi-view image data may facilitate identification and/or diagnosis of objects and/or conditions.

Cooling a Tool

FIGS. 9A-11 illustrate cooling a tool inside a living creature in accordance with some embodiments of the present invention. For example, a tool with a heat emitting part (for example an exothermic tool) may need cooling inside a lumen of a living creature. For example, a camera and/or a light source (for example a light emitting diode LED) may be cooled. For example a tube may supply cooling fluid flow to tool.

The fluid may be directed over a heat exchanger in thermal communication with the tool (for example the heat exchanger may include a heat exchange surface and/or a cooling fin and/or and outer surface of the tool and/or a Peltier element in contact with the tool).

Figure 9A:
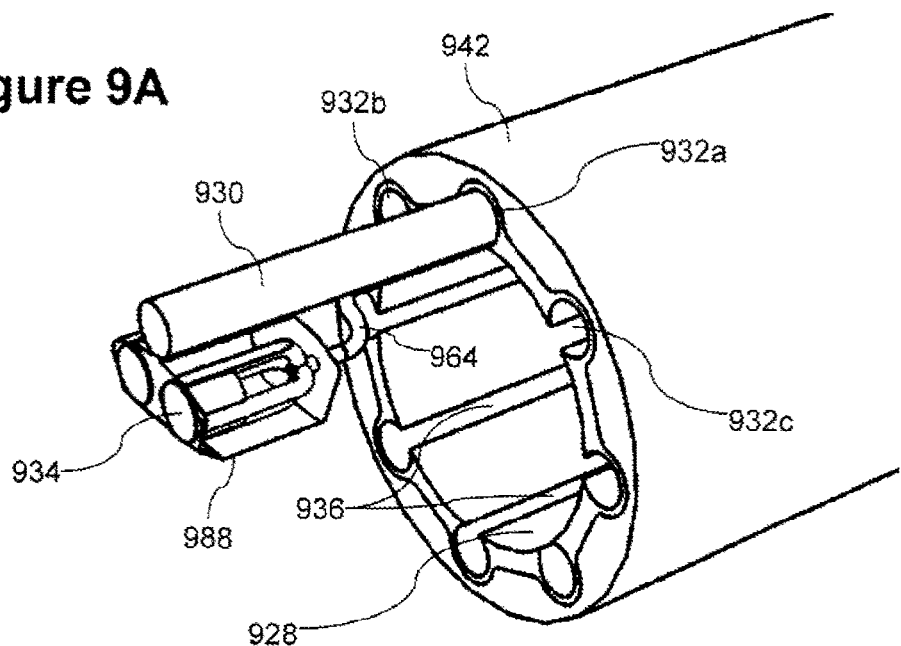
FIGS. 9A-B are perspective views of a tool cooling system in accordance with some embodiments of the present invention.
Figure 9B:
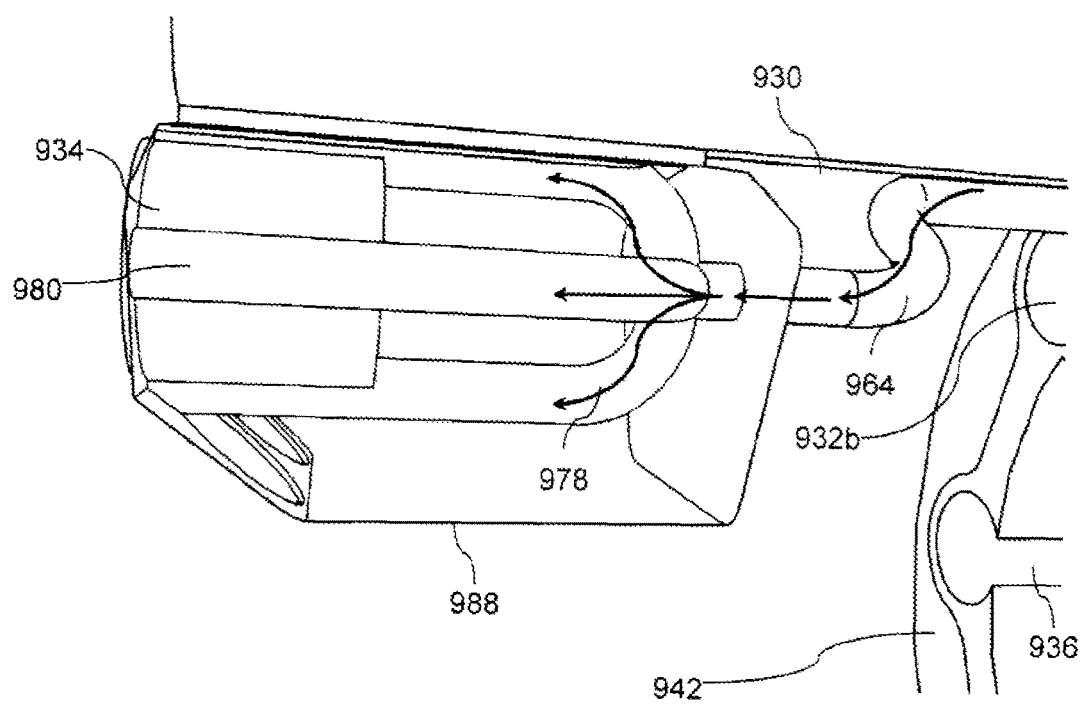

FIGS. 9A-B illustrate a tool being cooled accordance with an embodiment of the current invention. In some embodiments, cooling fluid flow 978 may be supplied from outside the living creature and/or be dumped into the living creature. For example, cooling fluid may include sterile saline solution and/or a medicine and/or a diagnostic chemical (for example a barium contrast medium) and/or a gas (for example air or carbon dioxide which may be in use for inflating an intestine during a catheter procedure). The fluid may optionally cool off the tool and then enter a lumen of the living creature. Alternatively or additionally, a body fluid may be drawn (for example by suction) from a location in the living creature (for example a location in the lumen in which the catheter is located) and/or cool a tool and/or may exit out of the living creature. Alternatively or additionally, fluid may be recirculated. Fluid may be suctioned out of a living creature, pass over a heat exchanger of the tool and/or returned into the creature. For example, cooling fluid may be pumped from outside the living creature to the tool and then back out the creature. Optionally, used cooling fluid may be discarded. Alternatively or additionally, used cooling fluid may be recycled. For example there may be a system for cooling the cooling fluid.

Alternatively or additionally, rather than pumping fluid through tube 964, a conductive heat sink may be used. Optionally the flow rate of the liquid and/or the temperature of the liquid may be selected and/or adjusted to achieve a desired level of cooling of the tool and/or a desired temperature of the liquid entering the lumen and/or a desired level of effect on the living creature. For example, if the tool is hot and the dosage of the material is low, then the flow rate may be raised. Alternatively or additionally, if the tool is heating and the dosage of the substance is already high, than the substance may be cooled before being introduced (improving cooling without increasing flow rate) or the concentration may be reduced and the flow rate increased (for medicaments for which the concentration can be reduced). For example the flow rate may range between 1 to 10 ml/min and/or between 10 to 50 ml/min and/or between 50 to 200 ml/min and/or between 200 to 1000 ml/min and/or between 1000 to 3000 ml/min. In some embodiments, in order to achieve a cooling effect, a fluid will be pumped into and out of a lumen at a balanced rate. For example a fluid may be pumped over a heat exchanger at a rate greater than minimal indicated for a medicinal effect. Excess material may be removed, suctioned out and/or vented out to achieve a desired net flow rate. For example, in the case of an intestine, in order to achieve a desired cooling, gas may be pumped over a heat exchanger into the intestine at a rate higher that that indicated for desired inflation of the intestine. In order to achieve a desired inflation of the intestine, a vent may be supplied to allow excess gas to be vented from the lumen.

In some embodiments, gas will be pumped into a lumen. For example, when the lumen is an intestine, air and/or carbon dioxide may be pumped into a lumen. For example the gas may keep the lumen inflated. The gas may optionally be passed over a tool needing cooling (for example an LED [light emitting diode]) and/or a cooling fin connected to a tool to cool the tool before being released into the lumen. Optionally the gas may be cooled before being pumped into the lumen.

In some embodiments, a carriage 930 may support tool 934. Optionally, carriage 930 is supported by a guide channel 932a. Optionally guides channels 932a-c communicate with working channel 928 through a longitudinal slit 936. Optionally carriage 930 may be twisted to deploy tool 934 away from an axis of a working channel 928. Optionally, cooling tube 964 passes from the proximal end of a sleeve 942 through carriage 930 and/or guide channel 932a to an inlet of housing 988a. A heat exchanger 980 of tool 934 may be located in the housing in contact with fluid flow 978. For example, heat exchanger 980 may include a cooling fin and/or a radiator and/or a cooling coil and/or a thin tube and/or another heat exchanger. Alternatively or additionally, cooling fluid may circulate within and/or around tool 934. For example tool 934 may be located inside of a housing 988a. Cooling fluid optionally enters an inlet of housing 988 and/or passes through a space in housing 988 and/or along the outside of tool 934. For example the housing may surround the tool on three sides and/or on four sides and/or on five sides and/or on six sides. For example the fluid may contact the tool on three sides and/or on four sides and/or on five sides and/or on six sides. Alternatively or additionally, cooling tubes may pass through working channel 928. Alternatively or additionally, a support carriage may pass through a first channel in an access channel (for example guide channel 932a and/or working channel 928) while coolant (for example a fluid) passes through one or more other channels (for example guide channel 932b and/or guide channel 932c and/or working channel 928). Alternatively or additionally, the heat exchanger may be located on the outside of the channel in a fluid flow zone, for example outside a flow inlet and/or outlet.

Alternatively or additionally a flow channel may pass through a tool cooling an inside of the tool.

Figure 10A:
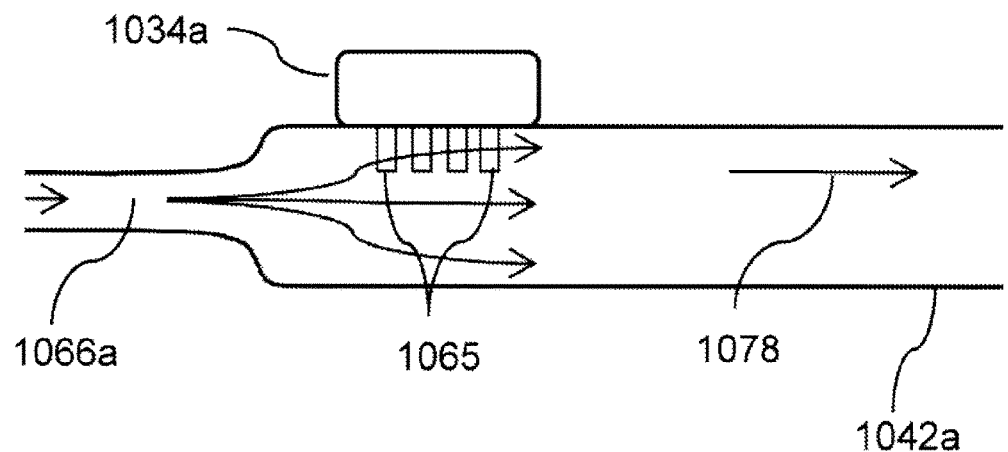
FIGS. 10A-B are schematic views of a tool cooling systems in accordance with some embodiments of the present invention.

FIG. 10A illustrates an embodiment of a system for cooling a tool using a fluid sucked from a lumen through an inlet 1066a in accordance with an embodiment of the present invention. For example, a suction tube 1042a includes a tool 1034a that requires cooling (for example a LED and/or a camera). A cooling fin 1065 is connected to tool 1034a. Optionally fin 1065 is in the suction flow 1078. For example fin 1065 may protrude inside tube 1042b. Optionally a part of tool 1034a is on the outside of tube 1042a.

Figure 10B:
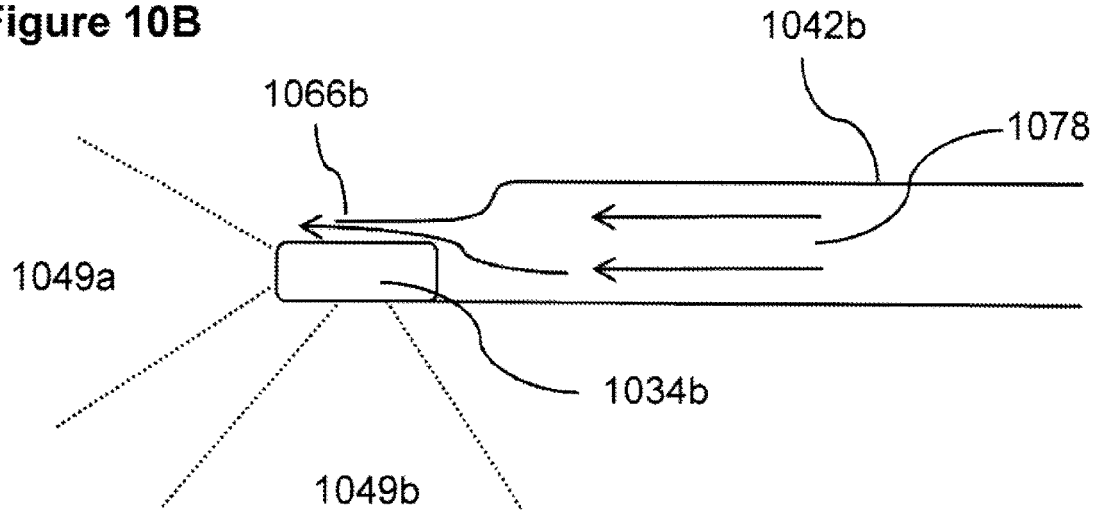

FIG. 10B illustrates a tissue washing system wherein irrigation fluid is used to cool a tool. Optionally, a tube 1042b is designed for insertion in to a lumen of a living creature. For example tube 1042b may be configured for insertion through a catheter channel. Fluid (for example air, carbon dioxide, saline solution and/or water) optionally flows 1078 from outside the living creature through in inlet (for example including tube 1042a) past a heat exchanger (for example fin 1065 and/or an outer surface of tool 1034b) to an outlet for example including a nozzle 1066b. Flow 1078 from nozzle 1066b may be focused on a structure needing cleaning. While fluid flows 1078 through tube 1042b it optionally passes over a heat exchanger of tool 1034b, cooling the tool. For example tool 1034b may include LED's producing light beams 1049a, b. For example, the heat transfer exchanger may include an outer surface of tool 1034b and/or a cooling fin. Optionally, the heat transfer surface may be included in a wall of tube 1042c.

Figure 11:
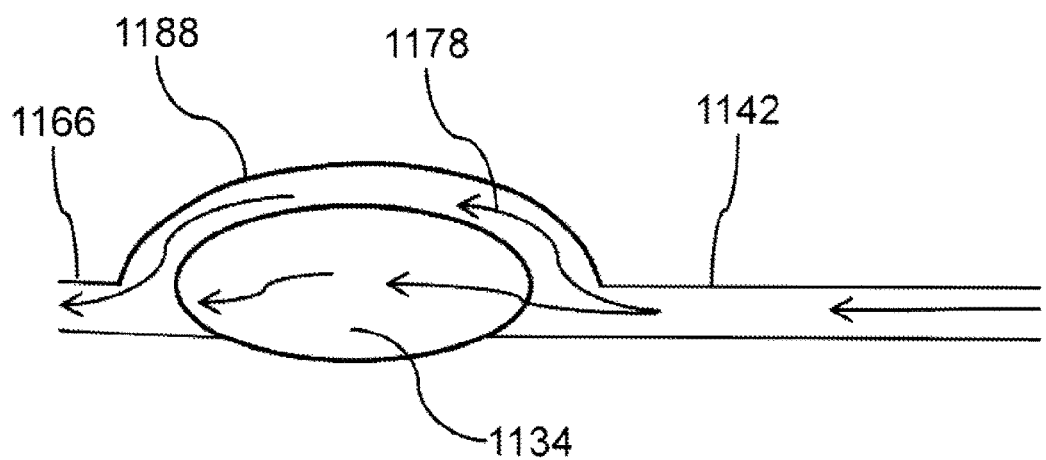
FIG. 11 is a schematic view of a tool cooling systems in accordance with an embodiment of the present invention.

FIG. 11 illustrates a tissue washing system according to an embodiment of the current invention. For example irrigation, fluid and/or medicine flows 1178 from a channel 1142 into a proximal inlet of a housing 1188 and/or around a tool with a heat emitting part, for example an exothermic tool 1134. Optionally, the fluid flow 1178 around the tool on 5 sides (for example around a proximal end, over a top, and/or around two sides). For example each side of the tool may include a heat exchanger which may be cooled by the fluid flow. Optionally the fluid then exits a distal outlet of channel 1142 and/or out a nozzle 1166.

Grinder

Figure 12:
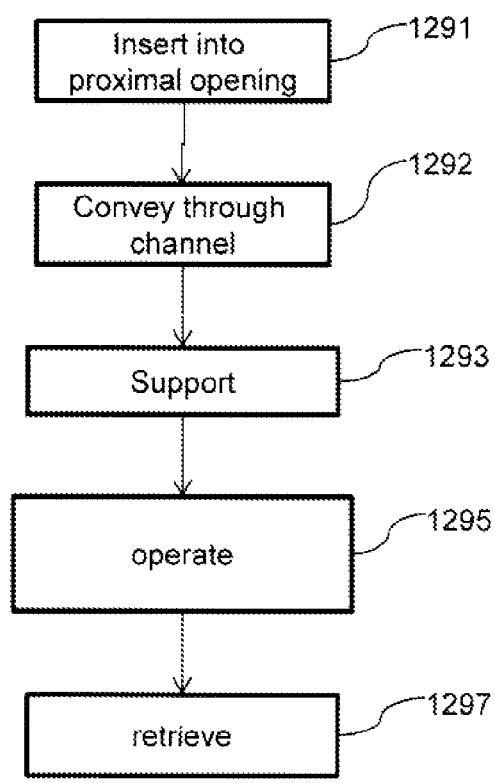
FIG. 12 is a flow chart illustration of a method of grinding body fluid entering a channel in accordance with an embodiment of the current invention.

FIG. 12 is a flow chart illustrating a method of grinding fluid suctioned from a lumen in accordance with an embodiment of the current invention. In some embodiments, a general purpose sleeve and/or catheter may be inserted into a lumen inside a patient. Optionally the catheter may be used for various diagnostic and/or therapeutic procedures. For example, when there is a need to suction fluid from the lumen, a grinder may be inserted 1291 into the proximal end of a channel of the catheter (for example the proximal opening of the channel may be located outside the patient) and/or conveyed 1292 through a channel of the catheter to a distal opening thereof (for example the distal opening of the channel may be located inside the patient). The grinder may be supported 1293 inside the channel and/or outside the channel. Optionally. As fluid is suctioned from the lumen into the channel, the grinder may be operated 1295 to grind lumps and/or solid matter entering the channel. Optionally, the grinder may be retrieved 1297 (for example by being conveyed through the channel and back out the proximal end of the catheter). Optionally, retrieving 1297 the grinder may free up the channel for further uses. For example, the catheter may remain in the lumen and/or may be used for conveying tools and/or materials into and/or out of the lumen and/or for controlling tools in the lumen.

Figure 13A:
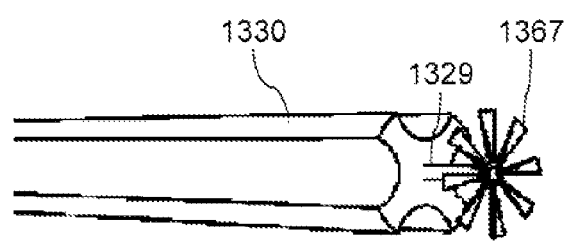
FIGS. 13A-B illustrate a grinder for body fluids suctioned into a catheter in accordance with an embodiment of the present invention.
Figure 13B:
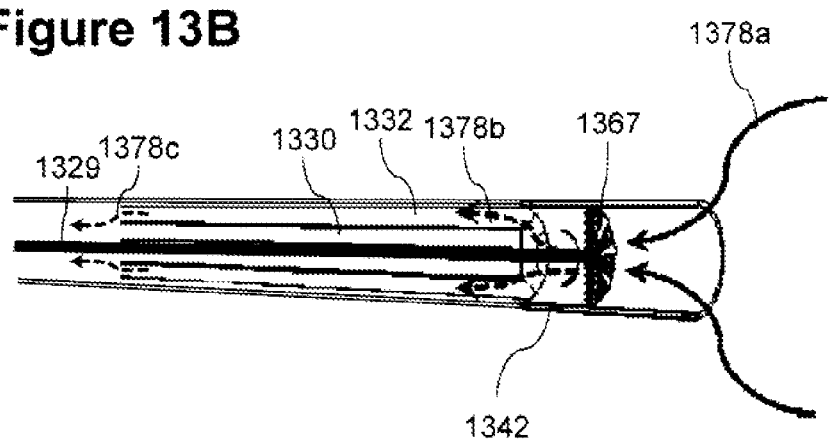

FIGS. 13A-B illustrate a grinder in accordance with an embodiment of the present invention. Optionally, the grinder is configured for insertion into a channel of a catheter. For example, the grinder blades may be inserted into a proximal opening of a catheter. The grinder is optionally conveyed along a channel of the catheter to a distal opening. At the distal opening the grinder breaks up lumps that may clog a lumen channel. The grinder optionally includes a transmission which transmits energy from a proximal end of the catheter to the grinder at a distal end of the catheter. The grinder is optionally supported by a carriage. For example the grinder may be connected to the distal end of the carriage and/or may be supported distal to the carriage. The carriage may be conveyed through a channel of the catheter. The carriage may optionally remain in the catheter channel while the grinder is in operation. The carriage optionally includes and/or defines sub-channels for conveying suctioned fluid from the distal opening of the catheter to the proximal opening. For example the sub-channels may run through the carriage and/or the sub-channels may be defined between the carriage and the walls of a channel of the catheter.

In some embodiments, a grinder may include a blade 1367 (for example blade 1367 may include a propeller) mounted to a carriage 1330. Carriage 1330 optionally supports blade 1367. For example, carriage 1330 aligns blade 1367 with the axis of the channel. For example, carriage 1330 limits lateral movement (movement perpendicular to the axis of the channel) of blade 1367. Optionally, blade 1367 is rotatable with respect to the catheter. Optionally carriage 1330 fixes the location of blade 1367 with respect to the length of the channel.

In some embodiments, carriage 1330 may fit snugly into a channel (for example preventing for example significant movement perpendicular to the axis of the channel) of a catheter (for example sleeve 1342). For example, carriage 1330 may fit a distal portion (for example within 1 cm of the distal end) of sleeve 1342. Alternatively or additionally, carriage 1330 may be fit along all and/or some (for example most) of the channel from a proximal opening (for example outside the lumen) to a distal opening (for example opening inside the lumen). For example, blade 1367 may be mounted rotatably to carriage 1330 via a shaft 1329. Alternatively or additionally, carriage 1330 may rotate the axis of catheter channel. Shaft 1329 and/or carriage 1330 may be rotated by a motor. For example the motor may be located outside the proximal opening of the catheter. Alternatively or additionally the motor may be located inside the channel of the catheter and/or outside the distal end of the channel.

Optionally, a sub-channel allows fluid flow from the distal opening of sleeve 1342 to the proximal opening thereof. For example the sub-channel may pass through carriage 1330. Alternatively or additionally, the sub-channel may be sandwiched between carriage 1330 and a wall of the catheter (for example as illustrated in sub-channel 1332 in FIG. 13B).

In some embodiments, fluid may flow 1378a (for example via suction) from a lumen into sleeve 1342. Alternatively or additionally blade 1367 may include a propeller. Spinning of the propeller may at least partially power flow 1378a. Flow 1378b optionally continues along sub-channels 1332 past carriage 1330. Flow 1378c optionally continues out the proximal opening of sleeve 1342.

In some embodiments, spinning of blade 1367 grinds solid particles and/or gels that flow 1378a into the distal opening a channel of sleeve 1342. Optionally blade 1367 may be located inside the channel. Alternatively or additionally, blade 1367 may be located outside the distal opening of the channel. For example blade 1367 may be located (inside and/or outside the channel) between 0 to 0.5 mm distant from the distal opening and/or between 0.5 to 1 mm of the proximal opening, and/or between 1 to 5 mm from the distal opening. Optionally blade 1367 may have a diameter between 60 to 90% of the width of the channel of the catheter and/or between 90 to 100% of the width of the channel of the catheter.

Frame for Catheter

FIGS. 14A-D illustrate frames for a catheter in accordance with some embodiments of the present invention. In some embodiments, a frame may include a spine directed along one edge of the catheter. The spine may be made up of joints and/or spacers. Elements of the frame may act a ribs connected to the spinal spacers and/or joints. The spacers may, for example, define the distance between elements in the region of the spacers. Elements of the frame may preserve the shape of the channels of the catheter (for example preventing the channels from collapsing).

Optionally, the spine of the frame may occupy a region along a single edge of the catheter. Limiting the cross section of the spine may allow for a variety of locations for channels along the cross section of the catheter. Channels may communicate with each other and/or with the outside of the catheter. For example a longitudinal slit may join a one channel to another channel and/or a channel to the outside of the catheter.

Figure 14A:
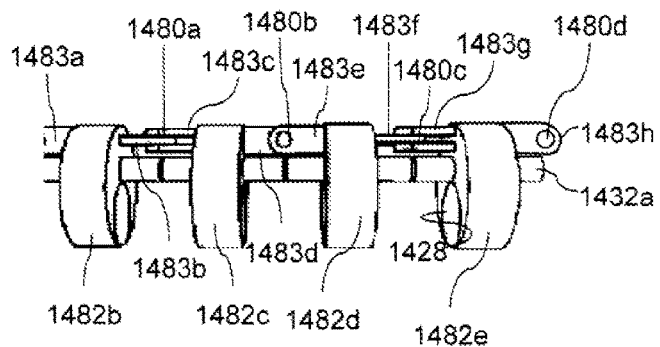
FIGS. 14A-D illustrate frames of a catheter in accordance with some embodiment of the present invention.

FIG. 14A illustrates a side perspective view of a catheter 1442 including a frame with a single spine in accordance with an embodiment of the present invention. In some embodiments, the spine of a frame may be made up of a series spacers 1483a-h joined by joints 1480a-d. Elements 1482b-e are optionally connected to the spacers 1483a-h and/or the joints 1480a-d.

In some embodiments, joints 1480a-d may include hinges which vary in orientation. The series of element may be bent in any direction by bending a combination of vertically oriented and horizontally oriented joints. For example, joints may be oriented in an alternating pattern. For example, joint 1480b, which is oriented to bend vertically around a horizontal axis intervenes for example between spacers 1483e and 1483d. Joint 1480a which is oriented to bend horizontally around a vertical axis intervenes for example between spacers 1483b and 1483c. Alternatively or additionally, some joints may bend in one direction (for example right) while others bend in the opposite direction (for example left). Optionally the end of the catheter (for example spacer 1483a) is raised by bending joints 1480b and/or 1480d. Optionally the end of the catheter (for example\1483a) is twisted rightward by bending joints 1480a and/or 1480c. Alternatively or additionally, joints may include ball and socket joints and/or flexible material and/or other joints. Optionally the length of the catheter and/or the spacing between elements 1482b-e may be fixed by the spine. For example bending of the catheter may be achieved by rotating elements 1482b-e around an axis on the spine. For example, the distance between elements 1482b-e in the region of the spine is optionally defined by the spacers. The distance between elements 1482b-e in the area not in the region of the spine is optionally adjusted according to steering of the catheter. For example, pulling a lower steering cable may cause the catheter to bend downward. For example, pulling the lower steering cable reduces the distance between elements at the bottom of the catheter while the distance between elements at the top of the catheter is preserved by the spacers of the spine (located at the center top of the catheter). For example, pulling a right steering cable may cause the catheter to bend rightward. For example, pulling the right steering cable reduces the distance between elements at the right side of the catheter while the distance between elements at the center of the catheter is preserved by the spacers of the spine (located at the center top of the catheter).

Optionally a frame may run the entire length of a catheter. For example, a frame may prevent collapse of channels, prevent twisting and/or limit turning all along the catheter. Alternatively or additionally, the frame may be located only near the distal end of the catheter. For example the frame may be located in distal region of length less than half of the catheter and/or less than ⅛ of the catheter and/or less than 1/16 of the catheter and/or less than 1/32 of the catheter and/or less than 1/64 of the catheter. For example the length of the framed region of the catheter may be less than 2 cm and/or less than 4 cm and/or less than 8 cm and/or less than 16 cm and/or less than 32 cm and/or less than 64 cm.

In some embodiments, the frame may assist steering of the endoscope.

Alternatively or additionally the frame may prevent collapse of channels, prevent twisting and/or limit turning along all and/or part of the endoscope, for example as the endoscope is maneuvered along a lumen. Maneuvering of the endoscope may be for example by steering cables and/or by actuators for example as described herein below and/or by any means known in the art.

Figure 14B:
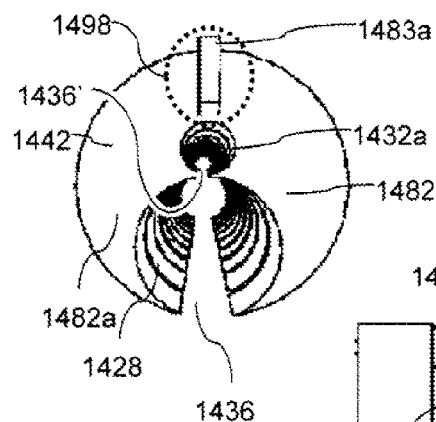

FIG. 14B illustrates a cross sectional view of a frame of a catheter in accordance with an embodiment of the current invention. In some embodiments, the spine of the frame may run along one edge of a catheter. For example in FIGS. 14A-C the spine is made up of joints 1480*a-d* which run along top (dorsal) edge of the catheter. Optionally the spine may be contained within a continuous convex region 1498 including for example less than 1/10 of the cross sectional area of the catheter. Alternatively or additionally the spine may be contained in a region of less than 1/64 of the cross sectional area of the catheter and/or 1/50 of the cross sectional area of the catheter and/or 1/36 of the cross sectional area of the catheter and/or ½5 of the cross sectional area of the catheter and/or 1/16 of the cross sectional area of the catheter and/or ⅑ of the cross sectional area of the catheter and/or ¼ of the cross sectional area of the catheter.

In some embodiments, the cross section of the catheter includes a working channel 1428. Optionally the working channel may include a longitudinal slit 1436 communicating with the outside of the catheter. Alternatively or additionally, a working channel may communicate through a second slit 1436' with a smaller guide channel 1432*a*.

Figure 14C:
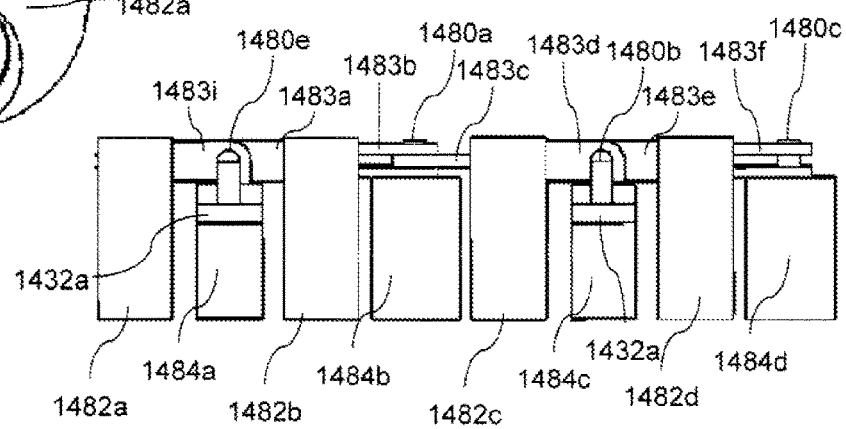

FIG. 14C illustrates a catheter frame with limiting inserts 1484*a-d* intervening between elements 1482*a-e*. For example insert 1484*a* limits downward twisting of element 1482*a* (for example as element 1482*a* twists downward insert 1484*a* intervenes between the bottoms of elements 1482*a* and 1482*b*, preventing joint 1480*e* from bending too far). For example insert 1484*b* limits sideways twisting of element 1482*a* (for example as element 1482*b* twists rightward insert 1484*a* intervenes between the right sides of elements 1482*b* and 1482*c*, preventing joint 1480*a* from bending too far). The minimum radius of curvature of bending of the catheter depends on the ratios of the dimensions of the parts of the frame. For example for a longer length of joint 1480*a* compared to the width (along the length of the catheter) of elements 1482*a*, 1482*b* and insert 1484*a*, the joint will be able to rotate more sharply.

Figure 14D:
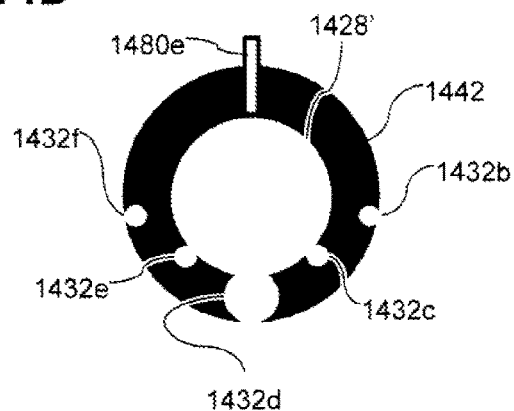

FIG. 14D illustrates an alternative cross section of a catheter with a frame in accordance with an embodiment of the present invention. In the embodiment of FIG. 14D, the frame has a spine running along the top of the catheter including a joint 1480*e*. The cross section optionally includes a large working channel 1428' and multiple smaller guide channels 1432*b-f*. For example guide channel 1432*d* has longitudinal slits communication with outside the catheter and also with working channel 1428'. For example guide channels 1432*e,c* have longitudinal slits communicating with working channel 1428'. For example guide channels 1432*b,f* include longitudinal slits communicating with the outer surface of the catheter.

Actuators for Steering an Endoscope

Figures 15A, 15B:
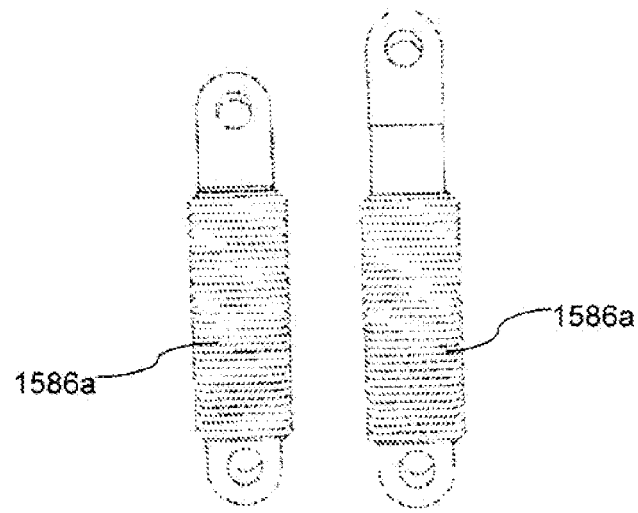
FIGS. 15A-B illustrate a magnetic actuator in accordance with an embodiment of the present invention.
Figure 15C:
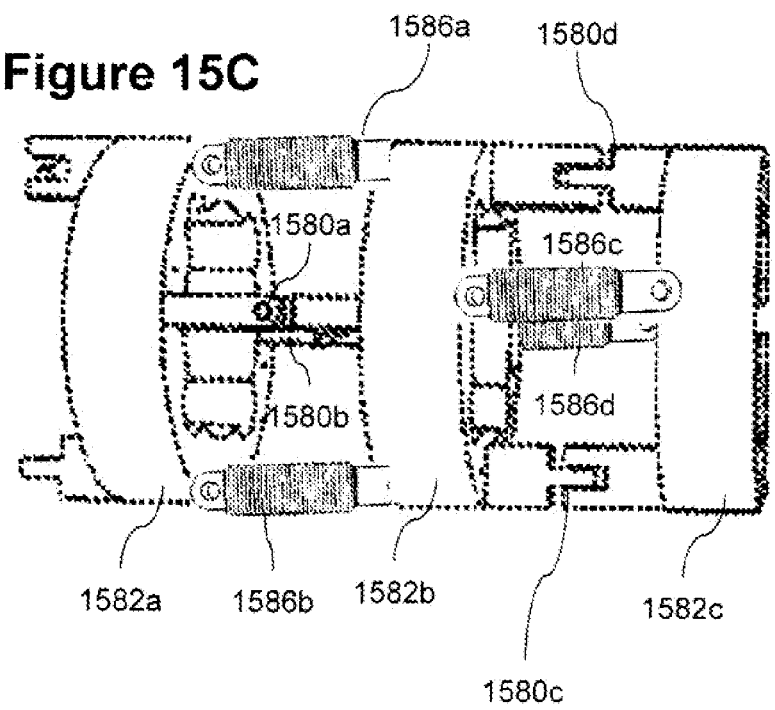
FIG. 15C illustrates a frame steered by magnetic actuators in accordance with an embodiment of the present invention.

FIGS. 15A-C illustrate the use of actuators for steering of an endoscope in accordance with an embodiment of the current invention. Actuators optionally allow independent control of various sections of an endoscope. In some embodiments, independent control may facilitate more precise steering of the endoscope than, for example, steering cables.

FIGS. 15A-B illustrate an exemplary magnetic steering actuator 1586*a* in a contracted and extended configuration respectively in accordance with an embodiment of the current invention. An operator optionally uses a remote control to contract or extend actuators inside a lumen of a patient.

FIG. 15C illustrates an endoscope frame made up of elements 1582*a-c* joined by joints 1580*a-d* and actuators 1586*a-d* in accordance with an embodiment of the present invention. Optionally, by selectively extending and/or contracting actuators 1586*a-d* an endoscope can be steered. For example to steer the end element 1582*a* upwards actuator 1586*a* would be contracted while actuator 1586*b* would be extended.

For example to steer the end element 1582*a* rightward actuator 1586*d* would be contracted while actuator 1586*c* would be extended. For example, each actuator may be one or more wires running to a power source outside the endoscope. Each actuator may be separately controlled by supplying a current to its respected wire.

Optionally a single wire may be connected to more than one actuator.

Alternatively or additionally, a controller may be located inside the endoscope.

The controller may control individual actuator according to control signals received from outside the endoscope. Use of a controller optionally reduces the number of wires running all the way through the endoscope.

Immobilizing an Endoscope

Figure 16A:
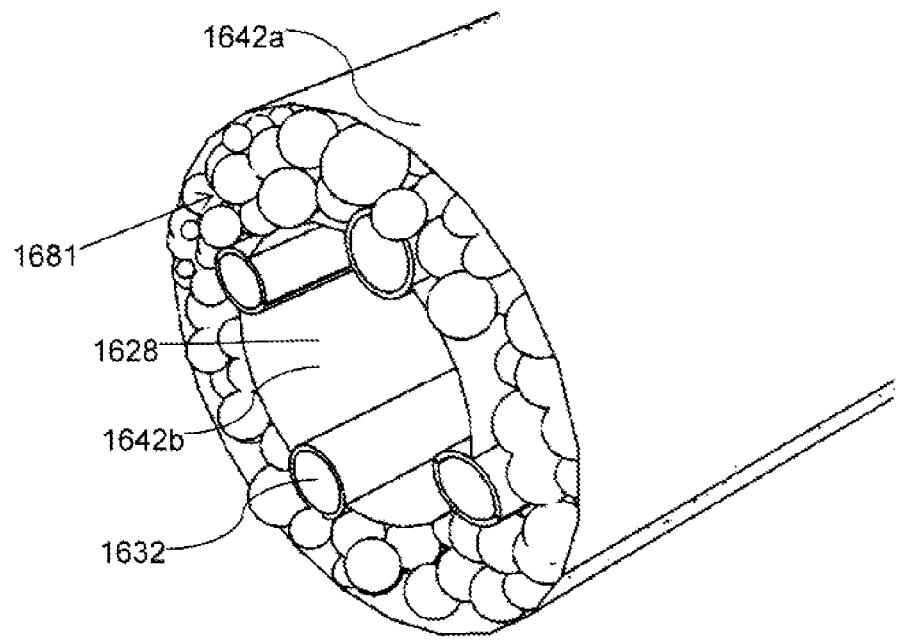
FIGS. 16A-C illustrate a joint immobilizer for a catheter in accordance with an embodiment of the current invention.
Figure 16B:
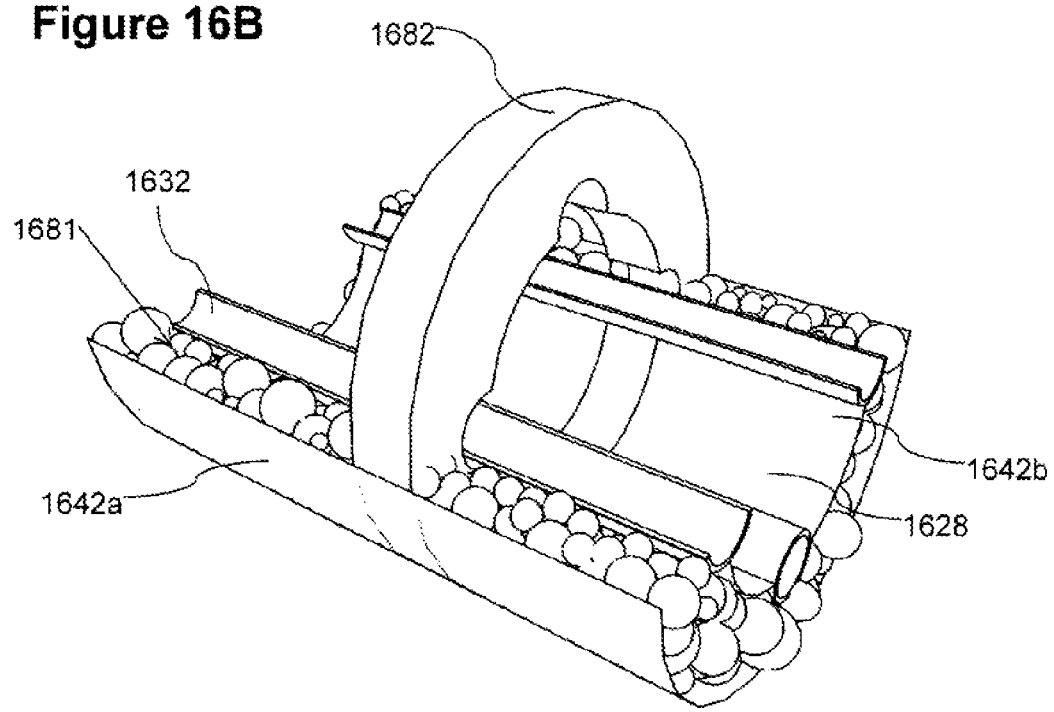
Figure 16C:
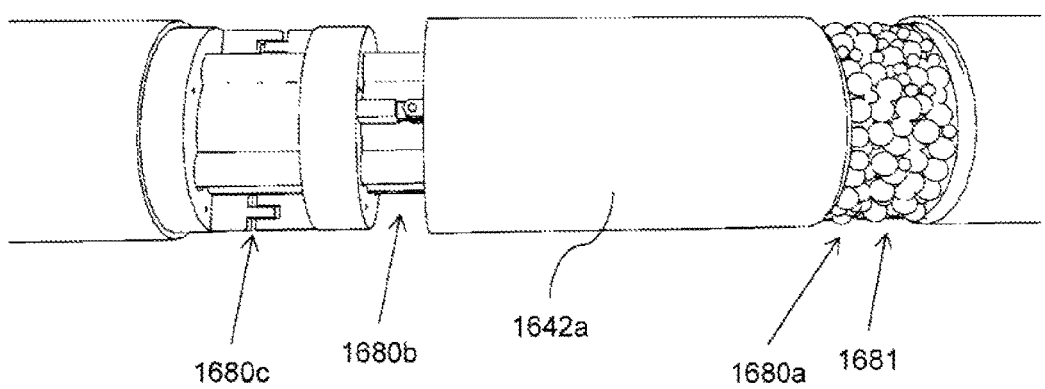

FIGS. 16A-C illustrate an endoscope with immobilizable joints in accordance with an embodiment of the current invention. For example an endoscope may be inserted into a desired location and/or configuration (for example a guide 1632 and/or a working channel 1628 may be inserted over a guidewire). The endoscope may optionally then be immobilized in place. Optionally the guidewire may then be removed with the endoscope remaining in place. Optionally the immobile endoscope may be used for access to the location and/or as a stable platform for tools in the location. Optionally the immobilization may be reversible. For example, after use, the endoscope may be remobilized and/or removed from the patient.

In the exemplary embodiment of FIGS. 16A-C, joints 1680*a-c* are reversibly immobilized by a collection of different sized balls 1681. Balls 1681 are optionally packed between frame elements (for example element 1682) and/or around joints 1680*a-c* and/or are sandwiched between two sleeves 1642a, b. Optionally, when balls 1681 can move freely, then as joints 1680a-c move, balls 1681 are redistributed.

Optionally, when the balls 1681 are immobilized, joint 1689a-c are optionally also immobilized. For example, a vacuum may be applied to the area where the balls 1681 are located collapsing the space between sleeves 1642a, b and/or immobilizing balls 1681 and/or joints 1680a-c. When air is allowed to enter between sleeves 1642a, b then balls 1681 and/or joints 1680a-c are remobilized.

FIG. 16A illustrates balls 1681 packed between two sleeves 1642a, b in accordance with an embodiment of the current invention.

FIG. 16B illustrates balls 1681 packed around a frame element 1682 in accordance with an embodiment of the current invention.

FIG. 16C is a cutaway illustration of balls 1681 packed around joints 1680a-c in accordance with an embodiment of the current invention. In FIG. 16C, outer sleeve 1642a is cut away around joints 1680a-c to illustrate the immobilizing system. Joint 1680a is illustrated with balls 1681 in place. Joints 1680b,c are illustrated with balls 1681 removed in order to better illustrate the joint.

It is expected that during the life of a patent maturing from this application many relevant technologies will be developed and the scope of the terms are intended to include all such new technologies a priori.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A catheter for transporting a tool between the outside of a living creature and a lumen inside the living creature, comprising:
    a working channel extending along a longitudinal axis of the catheter, the working channel including a proximal opening for allowing access from outside of the living creature and a distal opening for positioning inside a lumen of the living creature;
    at least one elongated guide extending along the catheter and of which a portion of the at least one elongated guide is in communication with a portion of the working channel;
    an outer sleeve extending along the longitudinal axis of the catheter, the outer sleeve comprising a mount to support a tool;
    a steerable frame that includes a spine extending along an edge of the catheter; and
    an immobilizing system including joints and a collection of different sized balls, wherein the joints are reversibly immobilizable by a collection of the different sized balls.

2. The catheter according to claim 1, comprising a slit for allowing communication between the portion of the at least one elongated guide and the portion of the working channel.

3. The catheter according to claim 1, wherein the elongated guide is narrower than the working channel.

4. The catheter according to claim 1, comprising a carriage connectable to the at least one elongated guide.

5. The catheter according to claim 4, wherein the carriage is flexible enough to follow curves in the working channel.

6. The catheter according to claim 4, wherein the carriage is configured to move the tool out of the working channel such that the working channel is unblocked for allowing the deployment of an additional tool.

7. The catheter according to claim 6, wherein the carriage is configured to mount the tool on the mount and to return the tool back into the working channel.

8. The catheter according to claim 1, wherein the carriage and the at least elongated guide are configured to allow conveying the tool through the working channel from outside the living creature to the lumen inside the living creature.

9. The catheter according to claim 1, comprising a tube configured to supply cooling fluid to a tool to be cooled, wherein the working channel is configured to receive the tool.

10. The catheter according to claim 9, comprising a heat exchanger for cooling the fluid.

11. The catheter according to claim 9, wherein the tube comprises a plurality of cooling tubes configured to surround the tool to be cooled.

12. The catheter according to claim 1, the spine comprising a series of elements that act as, ribs and further comprising spacers connecting the elements with each other.

13. The catheter according to claim 12, wherein the series of elements are connected with each other by a combination of vertically and horizontally oriented joints such that the series of elements are controllably bendable in any direction.

14. The catheter according to claim 12, wherein the balls are arranged such to be immobilizable by applying a vacuum where the balls are located to collapse the space between the elements, and wherein the balls are re-mobilizable by allowing air to enter between the elements.

15. The catheter according to claim 1, wherein the spine extends along a single edge of the catheter.

16. The catheter according to claim 1, wherein the steerable frame comprises frame elements, and the balls are packed between or around the frame elements.

* * * * *